United States Patent
Bates et al.

(10) Patent No.: US 6,273,861 B1
(45) Date of Patent: Aug. 14, 2001

(54) PNEUMATICALLY ACTUATED TISSUE SAMPLING DEVICE

(75) Inventors: James S. Bates, Bloomington, IN (US); John Haaga, Chagrin Falls, OH (US); Srinivas Nishtala, Bloomington, IN (US); Keith E. Hoffman, Spencer, IN (US); Harold G. Hawkins, Warsaw, IN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/145,201

(22) Filed: Sep. 1, 1998

Related U.S. Application Data

(63) Continuation-in-part of application No. 08/939,521, filed on Sep. 29, 1997, now abandoned.
(60) Provisional application No. 60/036,660, filed on Jan. 30, 1997.

(51) Int. Cl.$^7$ .................................................... A61B 10/00
(52) U.S. Cl. ........................ 600/567; 606/186; 604/506; 604/156; 604/164.12; 604/164.01
(58) Field of Search ..................................... 604/164–170, 604/256, 263, 264, 272, 274, 117, 507, 164.12, 156; 606/167, 170, 184, 185; 600/562, 564, 565–567

(56) References Cited

U.S. PATENT DOCUMENTS

| | | | |
|---|---|---|---|
| 4,680,027 | * 7/1987 | Parsons et al. | 604/68 |
| 4,953,558 | 9/1990 | Akerfeldt | 128/751 |
| 5,172,701 | * 12/1992 | Leigh | 128/753 |
| 5,195,533 | 3/1993 | Chin et al. | 128/754 |
| 5,213,110 | * 5/1993 | Kedem et al. | 128/754 |
| 5,234,000 | * 8/1993 | Hakky et al. | 128/754 |
| 5,282,476 | 2/1994 | Terwilliger | 128/753 |
| 5,312,023 | 5/1994 | Green et al. | 227/175 |
| 5,368,045 | 11/1994 | Clement et al. | 128/754 |
| 5,474,539 | * 12/1995 | Costa et al. | 604/164 |
| 5,480,388 | * 1/1996 | Zadini et al. | 604/165 |
| 5,544,670 | 8/1996 | Phillips et al. | 137/224 |
| 5,564,436 | * 10/1996 | Hakky et al. | 128/754 |
| 5,611,352 | * 3/1997 | Kobren et al. | 128/751 |
| 5,636,780 | 6/1997 | Green et al. | 227/176.1 |
| 5,711,472 | 1/1998 | Bryan | 227/175.1 |
| 5,817,033 | * 10/1998 | DeSantis et al. | 600/562 |
| 5,980,545 | * 11/1999 | Pacala et al. | 606/170 |
| 5,989,197 | * 11/1999 | Avaltroni | 606/567 |
| 6,197,041 | * 3/2001 | Shichman et al. | 606/185 |

* cited by examiner

*Primary Examiner*—Richard K. Seidel
*Assistant Examiner*—Jennifer Maynard
(74) *Attorney, Agent, or Firm*—Kenyon & Kenyon

(57) ABSTRACT

A novel instrument for automatic sampling or removal of tissue percutaneously from a patient. In a disclosed embodiment the instrument comprises a housing, a means for excising tissue from a target site within a patient's body extending from the housing, a means for impelling the excising means into a target tissue site in response to an impelling force, and a rotatable handle.

43 Claims, 11 Drawing Sheets

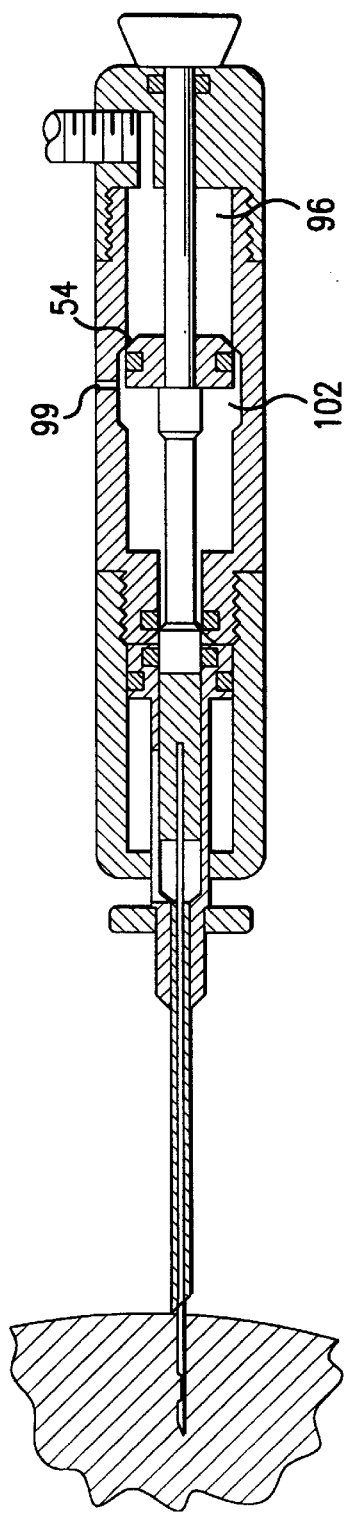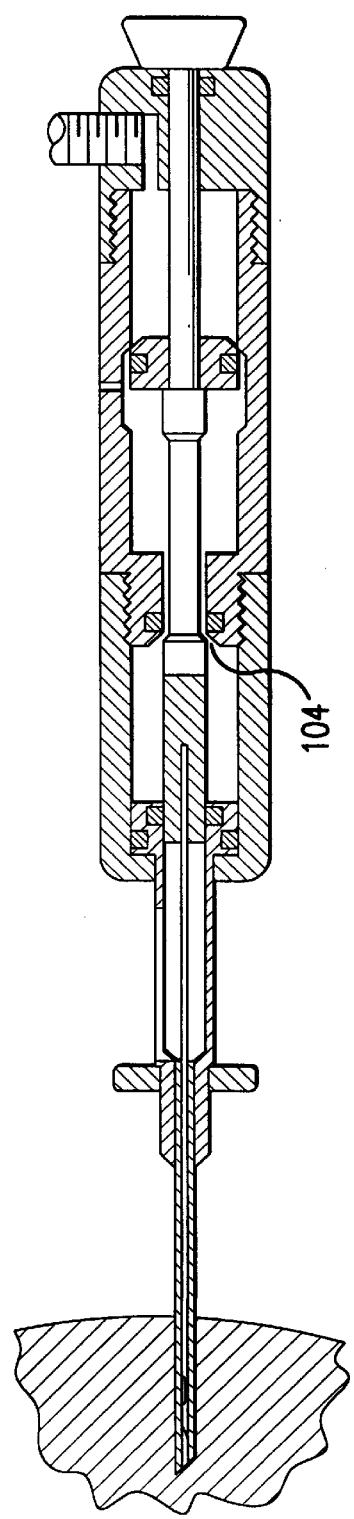

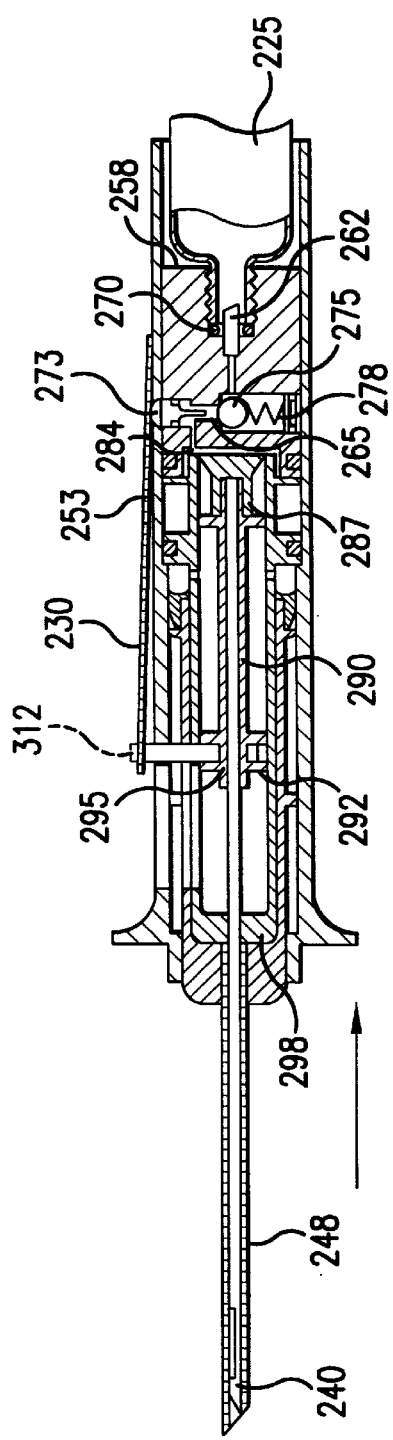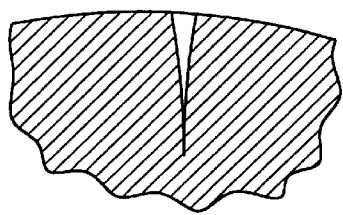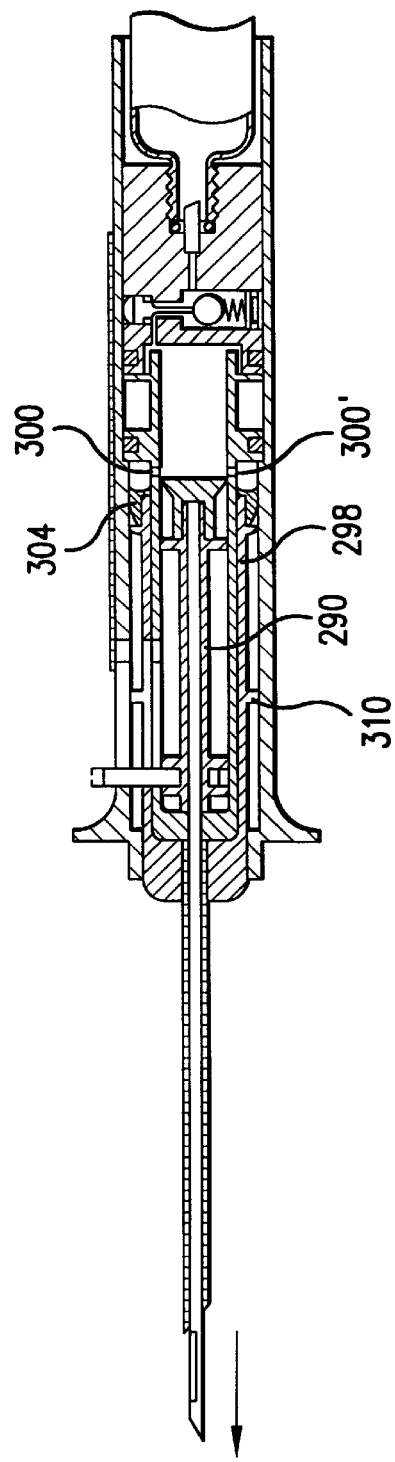

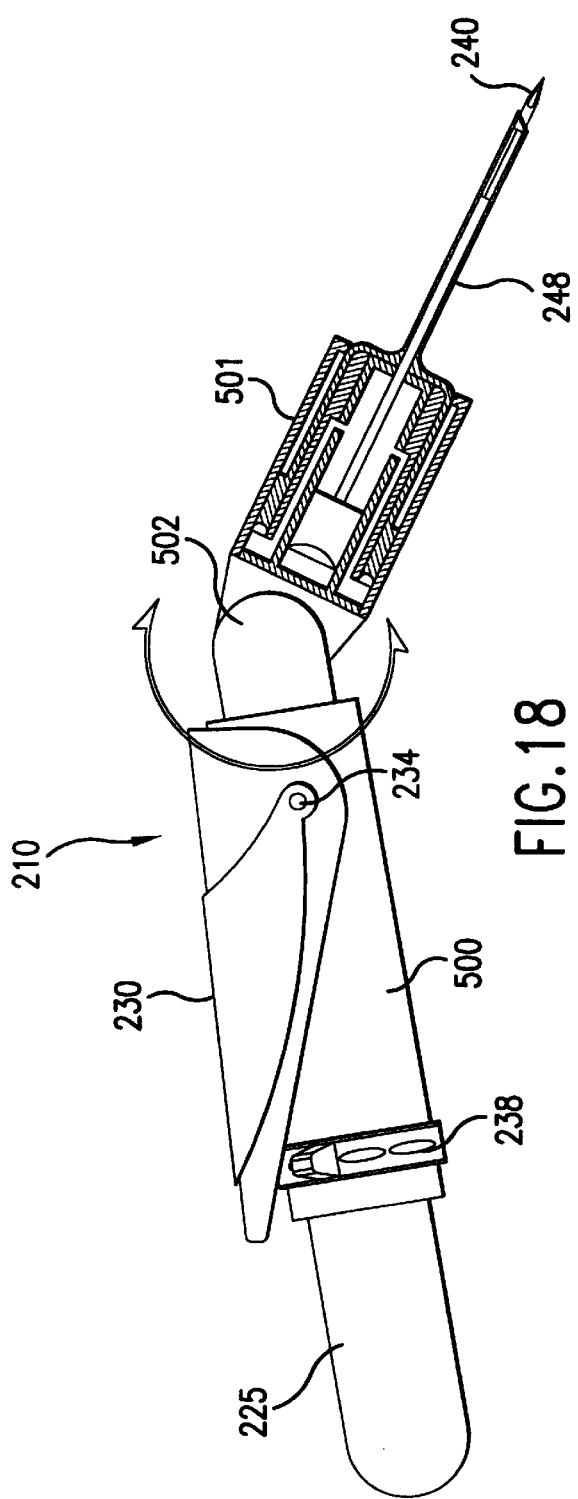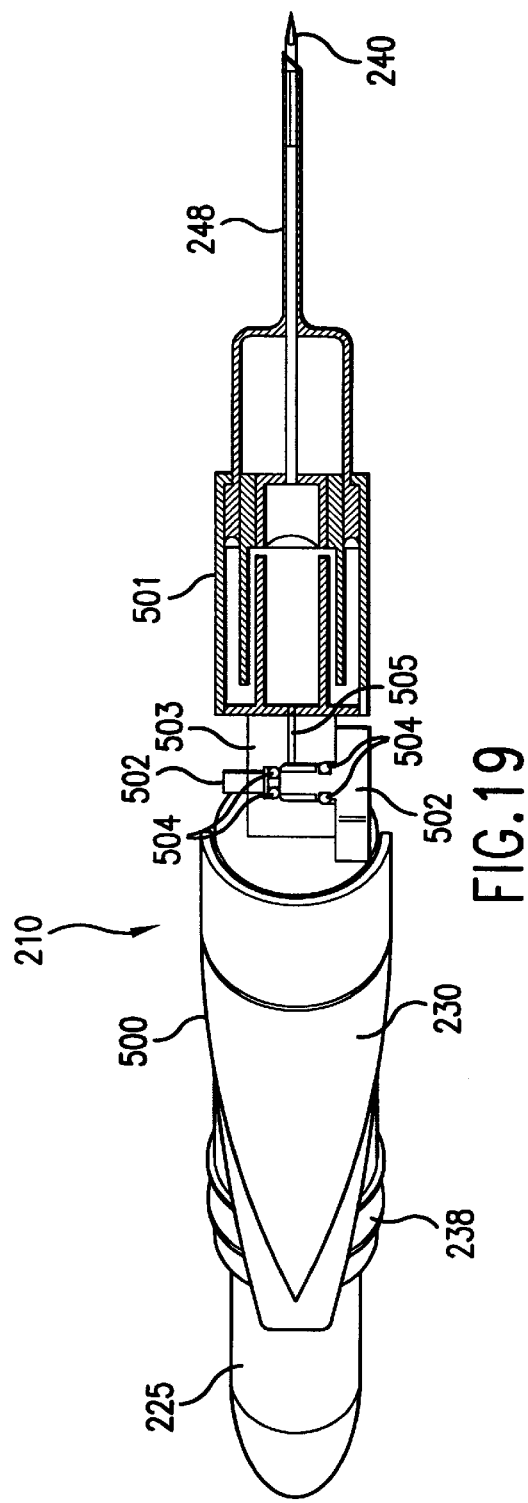
FIG.18
FIG.19

PNEUMATICALLY ACTUATED TISSUE SAMPLING DEVICE

This application is a continuation-in-part application of U.S. Pat. application Ser. No. 08/939,521, filed Sep. 29, 1997, and claims the benefit of U.S. Provisional Application Ser. No. 60/036,660, filed Jan. 30, 1997.

FIELD OF THE INVENTION

This invention relates in general to instruments for the automatic sampling of tissue from a patient. In particular, this invention relates to automatic tissue sampling or removing instruments actuated pneumatically.

BACKGROUND OF THE INVENTION

It is often desirable and frequently necessary to sample or test a portion of tissue from humans and other animals, particularly in the diagnosis and treatment of patients with cancerous tumors, pre-malignant conditions and other diseases or disorders. Typically, in the case of cancer, when the physician establishes by means of procedures such as palpation, x-ray or ultrasound imaging that suspicious circumstances exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy, on the other hand, is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section. The type of biopsy utilized depends in large part on circumstances present with respect to the patient and no single procedure is ideal for all cases. However, core biopsy is extremely useful in a number of conditions and continues to be used frequently by the medical profession.

To arrive at a definitive tissue diagnosis, intact tissue is needed from an organ or lesion within the body. In most instances, only part of the organ or lesion need be sampled. However, the portions of tissue obtained must be representative of the organ or lesion as a whole. In the past, to obtain tissue from organs or lesions within the body, surgery had to be performed to locate, identify and remove the tissue. With the advent of medical imaging equipment (x-rays and fluoroscopy, computed tomography, ultrasound, nuclear medicine, and magnetic resonance imaging) it has become possible to identify small abnormalities even deep within the body. However, definitive tissue characterization still requires obtaining adequate tissue samples to characterize the histology of the organ or lesion. For example, mammography can identify non-palpable (not perceptible by touch) breast abnormalities earlier than they can be diagnosed by physical examination. Most non-palpable breast abnormalities are benign; some of them are malignant. When breast cancer is diagnosed before it becomes palpable, breast cancer mortality can be reduced. However, it is often difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope. Prior to the late 1980's, reaching a definitive tissue diagnosis for non-palpable breast disease required a mammographically guided localization, either with a wire device, visible dye, or carbon particles, followed by an open, surgical biopsy utilizing one of these guidance methods to lead the surgeon to the non-palpable lesion within the breast.

Open surgical breast biopsies have many drawbacks. They can be disfiguring, expensive (in terms of direct costs to the patient and indirect costs to society from the patient being away from work), and are imperfect (the error rate for surgical biopsy has been reported to be from 2% to 22%). For example, a localization wire can be incorrectly placed by the radiologist. Even if properly placed, the efficacy of the biopsy may be marred by poor tissue selection by the surgeon, in which the lesion is not harvested. A properly harvested lesion may still suffer from the result of having the wrong section prepared for analysis.

Any of these errors will lead to an incorrect diagnosis of the lesion. Open surgical biopsies also carry a small mortality risk (due to the risks of anesthesia) and a moderate morbidity rate (including bleeding, infection, and fracture or migration of the localizing wire). In cases where multiple lesions are present in the breast, a surgeon is reluctant to biopsy each lesion due to the large tissue mass that must be extracted with each lesion. The most convenient lesion is taken which most often results in an incomplete diagnosis. Finally, all of this must be considered in the context of the frequency of procedures such as breast biopsies. In the United States, alone, it is estimated that open, surgical breast biopsies are performed on over 500,000 women annually. A less invasive alternative has long been sought.

A well known instrument used quite extensively for core biopsies in the past is manufactured by Travenol Laboratories of Deerfield, Ill., and is sold under the mark "TRU-CUT." This manual biopsy instrument at one time enjoyed as much as 98% of the market for such devices. As disclosed in U.S. Pat. No. 3,477,423, the instrument comprises a two-piece assembly: an outer cutting cannula mounted to one hub member and an inner stylet with a sampling notch ground into it mounted to a second hub, with the hubs being slidably interlocked. The instrument is assembled and placed into the body with the outer cutting cannula just to the rear of a lancet point or beveled distal end of the stylet. Upon inserting the device up to or in front of the area to be biopsied, advancement of the assembly is halted. The stylet is manually advanced distally of the cannula with the cannula held stationery. Upon advancement of the stylet, the specimen notch is exposed. Tissue surrounding the stylet prolapses into the specimen notch and the cutting cannula is then manually advanced distally over the stylet, slowly shearing off the tissue entrapped in the stylet's specimen notch. The instrument is then either (a) withdrawn and the stylet advanced distally to expose the tissue for preparation for study or (b) left in place and only the stylet is proximally removed from within the cannula so a determination of successful sampling may be made. If the sampling was not successful, the stylet may be reinserted into the cannula, which remains positioned within the patient, and an attempt to reposition the assembly of stylet and cannula and repeat sampling can be made.

Such a technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing the cannula. Another drawback is that the cannula is advanced relatively slowly, resulting in an extremely poor cutting action and allowing the surrounding tissue an opportunity to collapse, thus making no use of the stored kinetic energy in the material being severed. Further disadvantages are encountered when the tissue volume to be sampled contains areas of higher density than that of surrounding tissue, such as areas of calcification commonly associated with certain types of cancerous growths. A manually inserted sampling device is often incapable of penetrating the denser area of tissue which merely deflects the course of the cannula/stylet structure around the dense area and into the more compliant surrounding tissue.

In the late 1980's, two different stereotactic guidance systems were modified to allow the guiding portion of each system to accommodate spring powered devices such as the Biopty® (Bard Radiology) gun. As used herein, the term "gun" to refer to tissue sampling devices for "one-handed" operation refers to a design common to many of these devices wherein the shape of the device is adapted to fit the hand of a medical practitioner with a pistol-like grip, complete with a triggering mechanism. Free-hand ultrasound guidance techniques were also developed to guide the Biopty® gun to breast lesions detected by ultrasound. Although sold to perform a biopsy of the prostate, the "BIOPTY" gun and related "BIOPTY-CUT" needle have also been proposed for performing CT-guided abdominal biopsies. See Parker et al., "Technical Note: Adaptation of the Bard Prostate Biopsy Gun for CT-Guided Abdominal Biopsies," *CardioVascular and Interventional Radiology*, 12: 50–52 (1989); and Parker et al., "Image-directed Percutaneous Biopsies with a Biopsy Gun," *Radiology*, 171: 663–669 (1989). The BIOPTY-CUT 18-gauge needle is not adapted to be used apart from the BIOPTY gun, but needle placement is more cumbersome when the gun is attached. As contemplated by Parker et al., use of such devices can be adapted to a "three-hand" technique in which the medical practitioner's left hand manipulates a transducer for an imaging system; simultaneously, the practitioner's right hand grasps and guides the sampling device, typically at the base of the stylet/cannula assembly and forward of the handle portion of the device. When the practitioner is satisfied that the sampling device is properly positioned, he gives a "go" signal and the "third hand," belonging to a nurse or technician, triggers the sampling device in response to the practitioner's command.

Parker et al. describe a technique of placing the BIOPTY-CUT needle within the body before attachment of the needle to the gun. A short section of sterile plastic sheath is inserted around the cutting needle between the hub of the cannula and the hub of the cutting needle to maintain the two in fixed relationship; following placement of the BIOPTY-CUT needle, the needle is "pinned" to the skin before the gun is attached to avoid displacement of the needle tip longitudinally or introduction of unwanted angulation. The short section of plastic sheath is removed, and the needle hub assembly is then inserted into the spring-loaded sleds of the BIOPTY biopsy gun.

With image-guided percutaneous core breast biopsy, it should be possible to greatly reduce the number of open, surgical breast biopsies performed. However, there are limiting factors with image-guided breast biopsies. Manually operated two-step devices are awkward to manipulate, and the tissue samples obtained may often be unsatisfactory. The depths to which the stylet and the cannula are driven into the tissue mass must be carefully controlled for accuracy and efficiency. Caution is required, as well, in applying the force with which the stylet and cannula are plunged forward. Too little force may not sever the tissue sample from the mass; too much force may cause unnecessary damage to the surrounding vital tissues.

A variety of biopsy needles and guns have been described and used for obtaining tissue specimens. One such biopsy gun currently used is described in U.S. Pat. No. Re. 34,056, entitled "TISSUE SAMPLING DEVICE," issued to Lindgren et al. Additional examples of biopsy gun devices are disclosed in U.S. Pat. Nos. 4,600,014 and 4,958,625. The Lindgren Automatic Core Biopsy Device (ACBD) is an instrument which propels a needle set with considerable force and speed in order to pierce a tumor mass and collect the tissue sample. The ACBD has allowed physicians to accurately test tissue masses in the early stages of growth and has contributed to the medical trend of early diagnosis and successful treatment of cancer. The ACBD allows a biopsy to be performed on tumor masses as small as two millimeters in diameter. This procedure is performed under ultrasound or X-ray guidance. Tumors of this size cannot be biopsied reliably by hand since the tumor is about the same size as the biopsy needle. Manual attempts at biopsy often push the tumor away without piercing the mass. Automatic puncture devices are capable of accelerating the biopsy needle at such a velocity that even a small tumor can be pierced.

Such devices use a design comprising a handle held in a physician's palm, and a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. In an automatic mode of operation, the cannula, when in the retracted position, is spring loaded by means of a compressed spring. A release lever, which works against the compressed spring, is activated to release compression of the spring which then expands and pushes the cannula outwardly over the stylet. This instrument, as stated, requires two handed operation. Also, since the stylet is not removable proximally from within the handle, the entire instrument must be withdrawn to obtain access to the sample.

A fully automatic instrument manufactured by Radiplast, Inc. of Sweden is described in U.S. Pat. No. 4,699,154. This instrument comprises a reusable, spring-loaded box-shaped housing or handpiece, which activates a disposable cannula and stylet set. Both the stylet and cannula are activated in rapid succession. The instrument has the advantage of reducing the dexterity and motor coordination necessary in the use of manual devices and also eliminates the slow cutting action of the manually advanced cannula, replacing it with a very quick, clean cut. This instrument, however, also has its drawbacks. First, the reusable handpiece is very large, heavy, cumbersome, and expensive. They are also typically spring-powered devices and must be manually cocked with some sort of plunger bar. Such "cocking" of the gun requires considerable force and the gun must be cocked for each biopsy cut. When actuated, the springs provided in the gun accelerate the needles until a mechanical stop position is reached which can create a loud snapping noise and jerking motion which is a problem both to the physician and the patient. Its weight and the awkwardness in use preclude it from being used with imaging equipment other than ultrasound, inasmuch as it must be inserted into the body with the user maintaining control of the handpiece at all times. Thus, the patient cannot be imaged with many conventional radiographic apparatus, such as CAT scanners. A further drawback is encountered in automatically activating both the stylet and the cannula, as opposed to activating the stylet manually, in that the rapid speed at which the cannula follows the stylet into the tissue does not allow much tissue to collapse into the specimen notch, limiting the size of the sample.

Various attempts to overcome one or more of the disadvantages of the ACBD have been made. U.S. Pat. No. 5,183,052, entitled "AUTOMATIC BIOPSY INSTRUMENT WITH CUTTING CANNULA," issued to Terwilliger describes a biopsy instrument having a stylet and a cannula wherein the instrument urges the cannula past the stylet in order to collect a tissue sample and simultaneously causes a vacuum to be communicated to the cannula in order to assist the collection of the tissue sample by the cannula.

U.S. Pat. No. 5,183,054, entitled "ACTUATED BIOPSY CUTTING NEEDLE WITH REMOVABLE STYLET," issued to Burkholder et al., discloses a biopsy device having a tubular cannula through which a stylet, having a stylet cavity near the distal end, is placed. The stylet is removable from the cannula and removed from the biopsy device through the housing so that the tissue sample obtained by the biopsy device may be manually retrieved while the cannula remains in place within the patient, near the area being sampled. Thereafter, the stylet may be reinserted through the housing and cannula into the patient's tissue where additional tissue samples may be obtained. In this way, trauma to the tissue that ordinarily occurs upon reinsertion of the cannula and stylet is minimized.

U.S. Pat. No. 5,234,000, entitled "AUTOMATIC BIOPSY DEVICE HOUSING A PLURALITY OF STYLETS," issued to Hakky et al. describes a biopsy device for taking a plurality of samples of tissue from a living being. The device comprises a housing having a portion arranged to be held by a person using the device, a cannula having a proximal portion and a distal portion and being coupled to the housing. A plurality of stylets are located in the housing, with each of the stylets having a proximal end, a distal end, and a tissue receiving notch located adjacent the distal end. Each stylet is individually propelled through the cannula into the body so that a portion of the tissue prolapses into the notch. The Burkholder et al. and Hakky et al. devices share all of the disadvantages of needle-type devices with the exception that they are not limited to acquiring a single sample. In addition, transportation of samples by withdrawing stylettes from the instrument may compromise quality of the specimens through prolonged contact with the inside surface of the cannula.

U.S. Pat. No. 5,195,533, entitled "BIOPSY NEEDLE INSTRUMENT FOR STORING MULTIPLE SPECIMENS," issued to Chin et al. describes a biopsy needle instrument which includes a housing, an axially elongated stylet extending from the housing and a cannula coaxially extending from the housing and disposed about the stylet means. The stylet and cannula can move relative to each other and to the housing between extended and retracted positions. The stylet and cannula define, during a given operation, a specimen of a predetermined specimen axial length. The stylet includes means co-acting with the cannula for storing multiple, sequentially obtained specimens within the instrument. While multiple samples may be acquired with this device, there is no provision for separating the samples from each other or maintaining the integrity of the individual samples. In addition, the volume of tissue collected per entry into the body cannot exceed the capacity of the receiving notch.

U.S. Pat. No. 4,651,753, entitled "ENDOSCOPIC MULTIPLE BIOPSY INSTRUMENT," issued to Lifton, describes a biopsy instrument for use with an endoscope which includes a rigid cylindrical end attached to the distal end of a flexible arrangement of tubes. The rigid end comprises a cylindrical body having a cavity therein. The cavity extends towards the distal end of the body and is of size sufficient to hold plural samples therein. Inside the cylindrical body is a passageway which serves as a conduit for aspiration of tissue into the cavity and cylindrical body and a knife for cutting the tissue. Furthermore, a plunger is arranged coaxially with the knife for pushing individual biopsy samples into the distal end cavity of the cylindrical body. This device is clearly for endoscopic use and would be inappropriate for use in obtaining samples from a breast or organ interior. Although this device employs an active means to urge tissue into the receiving notch, it bears the same deficiencies as the Chin et al. device—the volume of tissue collected per bodily insertion cannot exceed the collection chamber volume, the origin of the samples cannot be differentiated, and the samples recovered must be manually handled for preparation.

When target tissue lies deep within patient, the need to utilize some form of imaging to direct the distal end of the biopsy system to the desired target further complicates the use of automated tissue sampling devices. Such imaging techniques, as mentioned above, may include fluoroscopic, ultrasound, CT scanning, or MRI equipment. If fluoroscopy is used, the large handle associated with mechanized biopsy guns may obscure visualization of the target and needle tip. When performing a CT guided biopsy procedure, the physician must check the progress of the biopsy instrument intermittently while it is advanced toward the target. Such CT guided procedures generally require the physician to release his or her grip on the biopsy instrument to allow the patient to be transported through the scanner for imaging. However, the bulk of the mechanized biopsy instruments described above do not allow scanning to occur because the patient and the biopsy instrument cannot both fit into the scanning aperture. Moreover, the weight of the handle housing for such devices is sufficient to deflect the outer cannula during scanning; therefore, the image that is obtained may not be an accurate indication of the direction of passage. The metal housing associated with some biopsy guns may degrade the CT scanned image by causing major artifacts, thereby limiting the physician's ability to, see the position of the needle in the patient. Even with respect to the previously mentioned BIOPTY-CUT needle placement method described by Parker et al. for use with the BIOPTY biopsy gun, the authors state that the length of the BIOPTY-CUT needle poses gantry clearance problems during CT scanning, and they further state that the act of attaching the gun to the needle after localization can be awkward. Moreover, as already noted, Parker et al. state that the BIOPTY-CUT needle must be "pinned" to the skin before reattachment to the gun.

Virtually all of the various automated biopsy instruments also tend to be heavy, difficult to manipulate, and incorporate biasing mechanisms which are either complicated in construction or require undue force to operate. Such limitations diminish the physician's control over the instrument and the precision with which biopsies may be performed. These instruments may be subject to inadvertent movement or torque which may, in turn, subject the patient to unnecessary trauma and risk. This is especially true of instruments which permit or require adjustment of the relative positions of any of their elements before the cannula is moved forward to sever the tissue sample. Similarly, the length of time required to perform a biopsy increases as the physician's degree of control of the instrument decreases, further elevating the risk to which the patient may be exposed. Finally, both physician and patient are exposed to the risk of inadvertent advancement of the cannula when the instrument is in its charged condition.

It should be evident from the discussion above that percutaneous biopsy techniques offer significant advantages over open biopsy procedures. It should be equally evident that these advantages have been significantly enhanced by the development of semi-automatic and fully automatic sampling devices, coupled with instrumental imaging guidance. However, the overall utility and efficacy of such techniques remain limited by certain constraining factors. As the discussion above has indicated, a major component of the advantage to be gained from the use of automatic spring-loaded sampling devices is the ability of the surgeon/practitioner to handle such devices with one hand, particularly when used in conjunction with hand-held imaging devices such as ultrasound. Thus, in this regard, it is essential that the design of such instruments must evolve within the physical constraints such use imposes.

Such design, of course, can benefit from the use of plastics and other lightweight materials, but limits remain in this area as well. With light weight there is generally an associated loss of strength. This translates into a form of compromise between the need for lighter and more compact designs with the need to provide sufficient compelling force to the sampling and cutting components of the sampling devices so that tissues with the widest possible range of densities can be sampled. It should be recognized here as well that there are other practical constraints on the amount of force that spring-driven sampling devices can bring to bear on the tissue to be sampled. Accepting that the ideal sampling device needs to be capable of one-handed operation, there is an upper limit to how much force biasing springs can exert and still be capable of being single-handedly cocked to the "ready" position for firing. At present this limit seems to be on the order of 8–10 pounds of force, due to the fact that the cocking force must usually be supplied by the practitioner's thumb while holding the device in a appropriate position as guided by the imaging system. The use of mechanical levering can provide an additional means to exert higher pressures even with one-handed operation, but this approach still faces limits in conjunction with spring-loaded devices. Use of levered triggering means also has the potential to add to the complexity of design, manufacture and use of such devices. Even if the maximum force conveniently exerted through one-hand operation can be extended to the 10–15 pounds of force range, the application of forces much beyond that range would almost certainly require two hands for setting or re-setting the device to the firing position.

The further practical effect of such constraints is that typical spring-loaded core biopsy devices must necessarily be limited to use in sampling soft tissues. Although significant uses remain in soft tissue sampling, there are other potentially beneficial applications not currently amenable to spring-loaded sampling devices. Thus, there is a need for automatic sampling devices that are lightweight and streamlined in design to permit facile one-handed operation; at the same time, there is a further need for devices that possess the mechanical strength necessary to incorporate impelling forces sufficient to enable sampling of tissues or cells characterized by greater density than that associated with the majority of typical soft tissue targets. At the same time such devices need to maintain mechanical simplicity as well, particularly in permitting the rapid re-arming and firing of the device for multiple tissue sampling. An additional factor in the design of such devices is the speed with which the actual sampling means enter and excise the desired sample tissue. It has been recognized that to achieve optimal sampling of target tissues with two-stage (stylet/cannula) designs, the speed of motion of the sampling means as it penetrates and excises target tissue can be critical. Thus, sampling force alone does not achieve optimal sampling. If the cannula/stylet action is too rapid, excision of target tissue is adversely affected. In summary, an ideal device would be simple in construction and operation, capable of the application of forces sufficient to sample a wide range of tissues, amenable to automatic operation, and provide optimal tissue sampling.

The inventors of the instant disclosure have discovered that compressed fluid may be utilized to actuate tissue sampling elements in sampling devices capable of both one-handed operation and impelling forces of sufficient magnitude to permit penetration and sampling of tissues with a wide range of densities. Accordingly, there is disclosed in detail herein an invention incorporating advantages addressing the specific requirements enumerated above. These and other advantages will be apparent through reference to the Detailed Description and Figures presented herein.

SUMMARY OF THE INVENTION

According to one aspect, the present invention provides a tissue removing device comprising a housing, a means for excising tissue from a target site within a patient's body extending from the housing, and a means for impelling the excising means into a target tissue site in response to an impelling force. In this aspect of the invention, the impelling means is contained within the housing where it is in fluid communication with a source of compressed fluid, and fluid from the source of compressed fluid provides the impelling force. Contemplated within this aspect of the invention is that the tissue to be removed is soft tissue such as tissue from a patient's lung, liver, kidney, thyroid, breast or muscle. Also contemplated is that the tissue to be removed is a dense tissue such as bone.

An important aspect of the invention is that the instrument can be held in and simultaneously operated by a single hand of a user. Furthermore, the invention contemplates an instrument wherein the impelling force is between 5 and 10 pounds. Also contemplated is an impelling force is between 7 and 9 pounds. Further contemplated is an instrument where the impelling force is between 15 and 25 pounds, or above.

In one embodiment, the tissue sampling device of the present invention contemplates the use of a stylet and a cannula to excise tissue from a target site within a patient and, further, where the stylet comprises a means for ensnaring tissue. Alternatively, the tissue sampling device of the present invention contemplates the use of a bone punch or other device capable of sampling tissue from denser tissue sites.

In one embodiment the invention contemplates the use of carbon dioxide gas as the compressed fluid. Alternatively, the compressed fluid can be air, nitrogen gas, or an inert gas. In various embodiments, the tissue sampling instrument of the present invention comprises a firing trigger wherein operation of the firing trigger releases fluid from the source of compressed fluid into the housing of the instrument. In one embodiment, the firing trigger is mounted directly to the housing. Alternatively, the firing trigger is remote from the instrument, and situated between the instrument and the source of compressed fluid.

In another embodiment, the tissue sampling instrument of the present invention comprises a housing where there extends from the housing an axially elongated stylet having a distal end and a proximal end and defining a specimen-defining formation adjacent the distal end, and a cannula coaxially disposed about the stylet, where the cannula has a distal end and a proximal end; and where the stylet and the cannula are mounted for axial movement relative to the housing and relative to the cannula between a first, retracted position and a second, extended position; means for individually impelling the stylet and the cannula distally toward the second, extended position of each in response to an impelling force, wherein the means is in fluid communication with a source of compressed fluid and fluid from the source of compressed fluid provides the impelling force; finger-displasable means for retracting the stylet and the cannula from their respective second, extended positions to their first, retracted positions, and where the instrument is constructed to enable release of the stylet to allow the stylet to move from the first, retracted position to said second, extended position and thereafter release of the cannula to allow the cannula to move from the first, retracted position to the second, extended position, and the finger-displasable means are selectively engaged by a finger or thumb of a single hand while the hand holds the instrument. Alternatively, the present invention contemplates an actuation switch wherein impelling of the sampling means as well as extraction and withdrawal of that sampling means is an integral operation and one that is triggered by a single switch function.

In another embodiment, the tissue removing device of the invention includes a head portion, a cannula extending from the head portion, a stylet extending from said head portion, a handle rotatably attached to the head portion, means for impelling said stylet toward an extended position in response to an impelling force, and means for impelling the cannula toward an extended position in response to an impelling force. The means for impelling the stylet and the means for impelling the cannula are in fluid communication with a single source of compressed fluid, and fluid from the source of compressed fluid provides the impelling force.

BRIEF DESCRIPTION OF THE DRAWINGS

FIG. 3 is a cross-sectional view of an embodiment of the present invention in which the stylet is in a position distal to the housing of the device.

FIG. 4 is a cross-sectional view of an embodiment of the present invention in which both the stylet and the cannula are in a position distal to the housing of the device.

FIG. 6 is a cross-sectional view of an embodiment of the present invention in which both elements of the tissue sampling means are in a retracted, ready to use orientation.

FIG. 7 is a cross-sectional view of an embodiment of the present invention in which the stylet is in a position distal to the housing of the device.

FIG. 18 is a top view of an embodiment of the present invention that includes a rotatable, detachable handle.

FIG. 19 is a side view of an embodiment of the present invention that includes a rotatable, detachable handle.

DETAILED DESCRIPTION OF THE PREFERRED EMBODIMENTS

Figure 1:
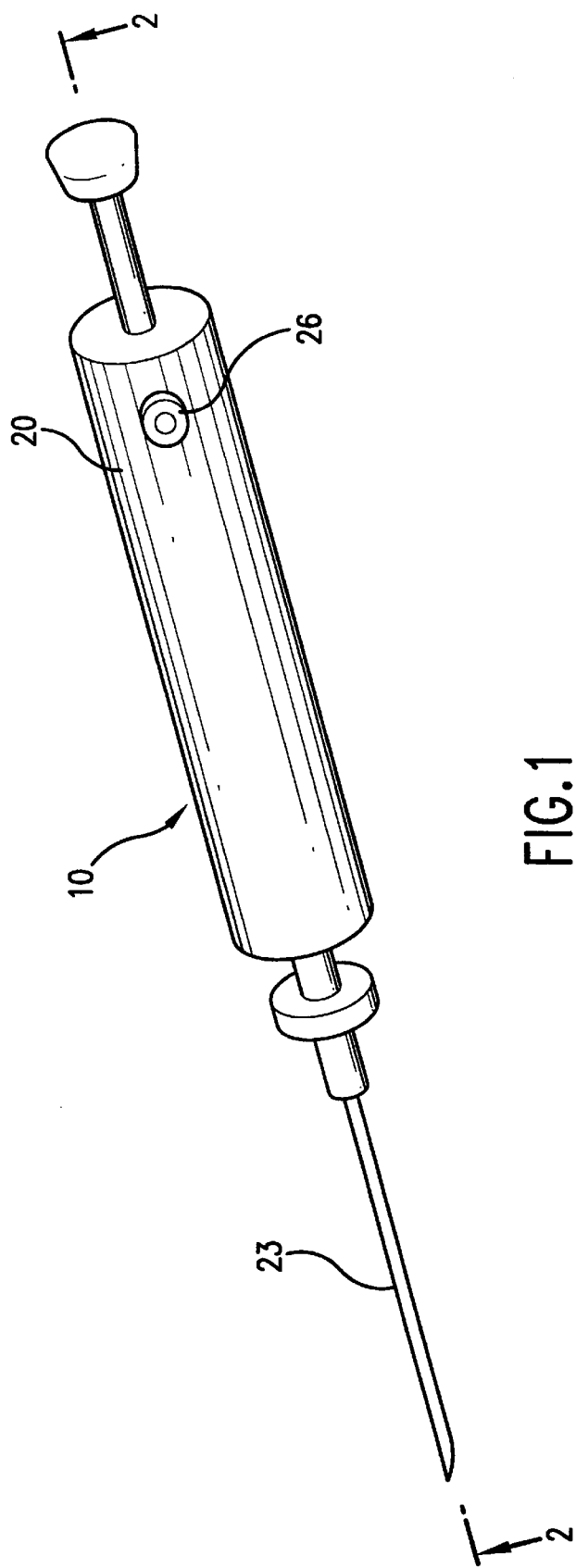
FIG. 1 is a perspective view of an embodiment of the tissue sampling instrument of the present invention.

Referring in general to FIG. 1, there is depicted at 10 a schematic representation of an embodiment of the pneumatically operated tissue sampling device of the present invention. The device consists of a housing 20 which is gripped in one hand by a surgeon/practitioner. Although presented schematically in a cylindrical geometry, it should be recognized that the housing 20 of the device may be fabricated in a variety of geometries. The sole constraint to the size and shape of the device housing 20 is that it must fit readily into the hand of the surgeon using it so as to permit facile one-handed operation. The material of construction is preferably chosen for lightness and ease of fabrication, while recognizing that unique aspects of the present invention permit the design of embodiments that utilize lighter and potentially less-expensive materials than would normally be associated with a design capable of impelling a sampling stylet, shown at 23, with sufficient force to pierce relatively dense tissue sources and, at the same time, operates at a speed that permits optimal tissue sampling.

Also depicted on the housing 20 of the device is a fluid access coupling 26 which provides a mechanical connection to the interior of the housing 20 for the compressed fluid which provides the impelling force for the operation of the device 10. Such a fluid may be any fluid capable of compression such that, upon the release of compressive forces, it expands into the inner valved structure of the housing 20 with sufficient force to drive the dual piercing elements of the device 10 into the target tissue of choice. A preferred fluid would be compressed carbon dioxide gas ($CO_2$).

Although not depicted in FIG. 1, the source of the compressed fluid may be remote from the device 10 and the fluid access coupling 26. In such a configuration it is contemplated that the source of compressed fluid would be of relatively large volume so as to easily supply sufficient fluid to fill the volume of the connecting means (not shown in FIG. 1) between the source and the fluid access coupling 26. It is further contemplated that in such a configuration the compressed fluid may be compressed air or some other mixture of inexpensive and non-combustible gases. Alternatively, the source of compressed fluid such as $CO_2$ may be a small, self-contained cylinder such as that used with air-powered rifles or bicycle tire inflation devices. If such a source of compressed fluid is used, then it would be preferred that the cylinder be mounted either on the housing 20 of the device, or in close proximity so as to minimize the loss of useful gas compression that would arise from filling the volume of the connecting means between the fluid source and the fluid access coupling 26.

Figure 2:
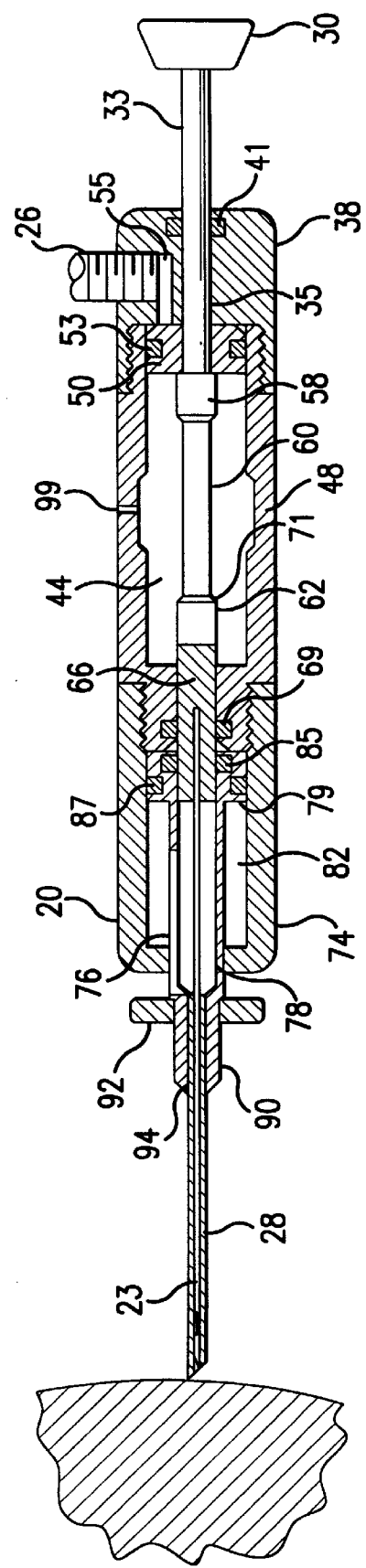
FIG. 2 is a cross-sectional view of an embodiment of the present invention in which both elements of the tissue sampling means are in a retracted, ready to use orientation.

Referring now to FIGS. 2–4, there are depicted section views of an embodiment of the device 10 of the present invention, along the plane 2—2, through the longitudinal axis of the device as indicated from FIG. 1. FIG. 2 is a representation of this embodiment of the present invention in a fully retracted mode wherein the sampling stylet 23 and the cannula 28 are poised for triggering into the selected tissue site. FIG. 3 is a representation of the device after triggering the release of the stylet 23 wherein the stylet is in a fully extended position, but the cannula 28 has not yet been triggered for release. FIG. 4 is a representation of this embodiment of the device wherein both cannula 28 and stylet 23 have been triggered and are in the fully extended position.

Referring now to FIG. 2, the stylet 23 and the cannula 28 constitute a set of piercing and cutting instruments the controlled operation of which enable the sampling of tissue in accord with the practice of the present invention. As can be seen from FIGS. 2–4, stylet 23 and cannula 28 are co-axial and parallel to the long axis of the housing 20 of the tissue sampling device 10. In the fully retracted position as shown in FIG. 2, the stylet 23 is completely within the cannula 28 that extends forwardly from the distal end of the housing 20 of the device. Moving attention to the opposite, proximal end of the device, there is shown a stylet retracting knob 30 which is attached to the proximal end of the upper stylet shaft 33. The upper stylet shaft 33 is aligned coaxially with the long axis of the device 10 and extends through a shaft conduit 35 through the upper housing cap 38 of the housing 20 of the device. Located toward the proximal end of the shaft conduit 35 there is the upper stylet o-ring 41 which provides a fluid-tight seal between the outer walls of the upper stylet shaft 33 and the inner walls of the shaft conduit 35. As will be recognized by one of skill in the appropriate art, the use of such an o-ring configuration allows for a fluid-tight seal between the inner volume of the device housing 20 and the external atmosphere, while at the same time allowing for facile movement of the stylet shaft 33 within the upper housing cap 38. It will be further recognized that the tolerances and other design criteria of such sealing mechanisms will vary depending on whether the fluid that provides the impelling force to drive the stylet/cannula mechanism is a liquid or a gas. However, the present design is readily adaptable to use of either type of fluid. The upper stylet o-ring 41, as well as the other o-rings utilized in the construction of this embodiment of the present invention, may be constructed of any material compatible with the material of construction of the other structural elements of the device, bearing in mind the expected fluid pressure ranges within the device during operation. Suitable materials for such o-rings would be EPDM rubber (ethylene propylene diene monomer), nitrile, butyl, thermoplastic elastomer, or silicone, with the preferred material being EPDM.

The upper stylet shaft 33 extends through the upper housing cap 38 and into the upper cavity 44 of the central housing portion 48 of the device. At the distal end of the upper stylet shaft 33, there is a stylet piston collar 50, the outer walls and upper surface of which cooperatively engage the inner walls of the central housing portion 48 of the device and the lower inside surface of the upper housing cap 38. In a currently contemplated embodiment of the present invention, the stylet piston collar 50 is approximately 0.5 inches in diameter. By way of example, current spring-actuated sampling devices of this general nature are limited to an actuation spring pressure of approximately 8 to 10 pounds. In contrast, the fluid-actuated design of the present invention is capable of supplying compelling forces as high as fifty pounds, or more. The higher forces of which the present invention is capable offer significant advantages not possible with the spring-actuated devices of the prior art.

Disposed circumferentially around the outer walls of the stylet piston collar 50 and retained within an appropriate circumferentially-disposed cavity therein, is the stylet piston o-ring 53. This o-ring provides a fluid tight seal between the inner walls of the central housing portion 48 of the device and the stylet assembly as, upon triggering, it moves through the central housing portion of the device. On the circumferential edge of the upper surface of the stylet piston collar 50 there is disposed a bevel 54, as can be seen more clearly in FIG. 3. The angled surface of the bevel 53 creates appropriate fluid flow passages within the device as the device is triggered for sampling, as will be described in more detail below.

As can be seen from FIG. 2, the upper surface of the stylet piston collar 50 engages the inner surface of the upper housing cap 38 when the stylet is in the fully retracted, ready for firing position. In this position, access to or from the upper cavity 44 through the upper fluid flow channel is effectively blocked. In this fashion, fluid from a pressurized fluid source that gains access to the device through the fluid access coupling 26 is restrained from entering the inner volumes of the device until the action of the device is triggered. In like fashion, fluids from within the upper or lower housing portions are retained within, through action of the fluid tight seal of the o-ring. In operation, there is a pressure relief outlet 99, normally closed, that permits the release of excess fluid pressure. At the distal end of the upper stylet shaft 33 there is an upper transitional collar 58 through which the upper stylet shaft is joined to the central stylet shaft 60. At the distal end of the central stylet shaft 60 there is the lower transitional collar 62 through which the central stylet shaft is joined to the lower stylet shaft 66. The proximal end of the stylet 23 is embedded in and coaxial with the distal end of the lower stylet shaft 66.

Disposed circumferentially about the inner walls of the distal end of the central housing portion 48 of the device, and retained within an appropriate circumferentially-disposed cavity therein, is a housing o-ring 69 that provides a fluid tight seal between the inner walls of the central housing portion 48 and the outer walls of the lower stylet shaft 66 as it moves through the housing 20 of the device. On the circumferential edge of the upper surface of the lower transitional collar 62 there is disposed a shaft bevel 71. The angled surface of the shaft bevel 71 creates appropriate fluid flow passages within the device as the device is triggered for sampling, as will be described in more detail below.

Disposed within the lower housing portion 74 of the device there is the upper cannula shaft 76. The upper cannula shaft 76 is comprised of a central stylet conduit 78 co-axial with the stylet 23 and through which the stylet 23 passes. On the proximal end of the upper cannula shaft 76 there is a cannula piston collar 79, the upper surface of which engages the lower surface of the central housing portion 48 of the device. In the fully retracted position as shown in FIGS. 2 and 3, the lower cavity 82 of the device housing 20 is a completely enclosed, fluid-tight volume. Toward the proximal end of the cannula piston collar 79, there is, disposed circumferentially about the outer surface, and retained within an appropriate circumferentially-disposed cavity therein, the upper cannula piston o-ring 85 that provides a fluid tight seal between the inner walls of the central stylet conduit 78 and the outer surface of the lower stylet shaft 66. Distally of the upper cannula piston o-ring 85 there is the lower cannula piston o-ring 87 disposed circumferentially about the outer surface of the cannula piston collar 79, and retained within an appropriate circumferentially-disposed cavity therein. This o-ring provides a fluid tight seal between the outer surface of the cannula piston collar 79 and the inner walls of the lower housing portion 74 of the device. Circumferentially disposed about the outer surface of the cannula shaft 90, external to the distal end of the device body 20, is a cannula retraction collar 92.

The cannula 28 is positioned within the external cannula shaft 90 in a cannula channel 94 that is co-axial with the cannula 28, stylet 23 and other longitudinally-oriented components of the device 10. Also apparent from FIGS. 2–4 is that the housing 20 of the device is composed of three separate portions, the upper housing cap 38, the central housing portion 48, and the lower housing portion 74. The upper housing cap 38 has a distally-disposed recess 96, as can be seen more clearly in FIG. 3, the inner walls of which are threaded to engage correspondingly-threaded outer surfaces of the proximal end of the central housing portion 48. In a like manner, the outer surface of the distal end of the central housing portion 48 is threaded to engage correspondingly threaded inner surfaces of the proximal end of the central bore of the lower housing portion 74. In this manner, the housing 20 of the device of this embodiment of the instant invention can be easily assembled and disassembled to permit facile interchange of stylet and cannula sets, as well as cleaning and/or sterilization of the housing portions.

Figure 5:
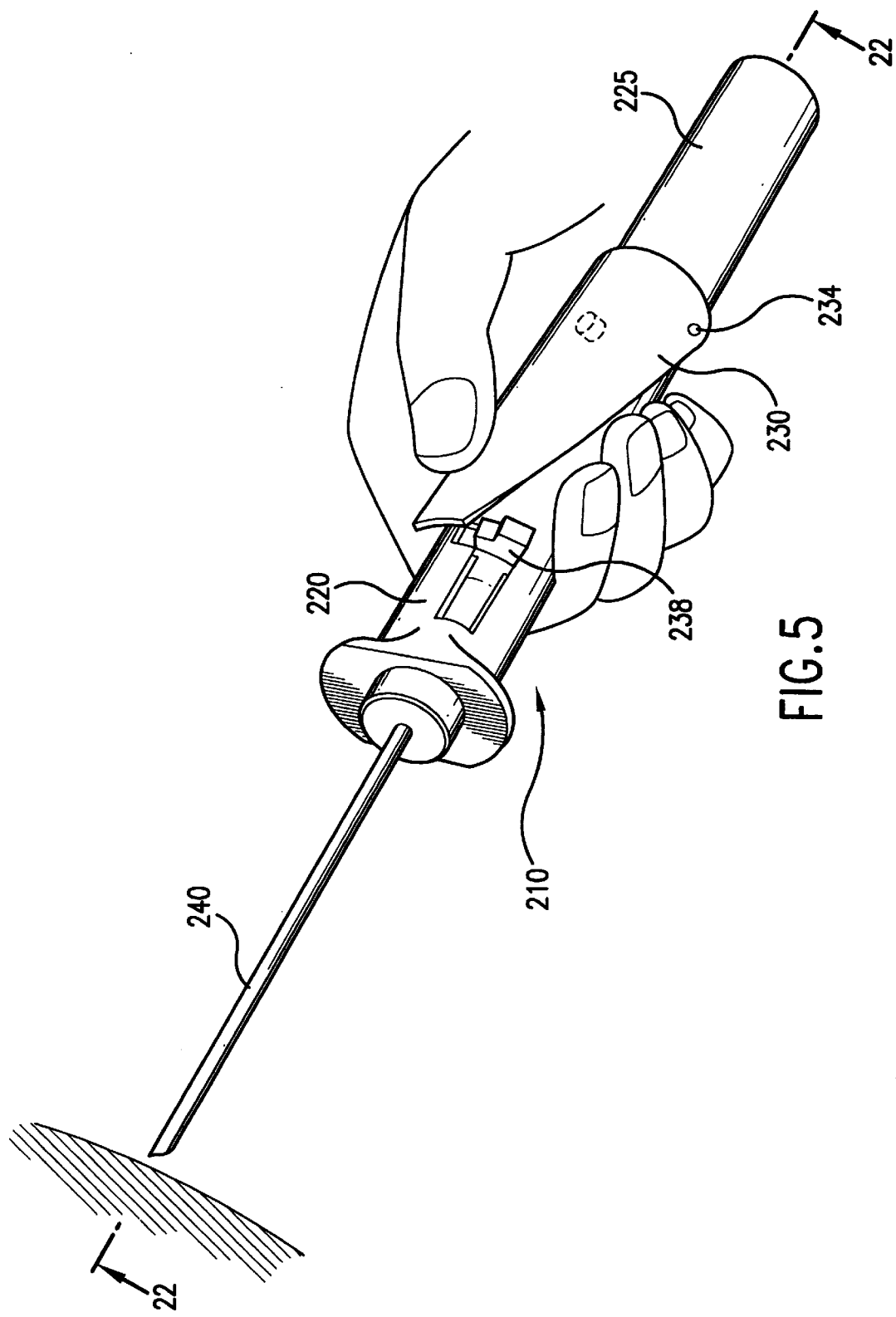
FIG. 5 is a perspective view of a specific alternative embodiment of the tissue sampling instrument of the present invention.

A specific alternative embodiment is depicted generally in FIG. 5 at 210. As shown, the sampling device 210 is depicted with a cylindrical body 220, although it will be recognized that such a cylindrical configuration is depicted for convenience sake only, and is not intended to be in any way limiting of the geometries that such a device may assume. The primary requirement for the geometry of the device is that it must fit comfortably within a surgeon/practitioner's hand for facile one-handed operation. In the embodiment depicted in FIG. 5, the source of compressed fluid is a compact cylinder of compressed carbon dioxide gas shown at 225. In the embodiment depicted in FIG. 5, the gas cylinder 225 is threadably engaged into the proximal end of the device body 220, forming a linear extension of that body, although it should be recognized that other configurations for placement of the compressed fluid source would be possible, consistent with alternative geometries for the device body 220. Also pictured in FIG. 5 is the firing trigger 230 which is connecting by a pin hinge 234 to the device body 220 toward the proximal end of that body. The distal end of the firing trigger 230 is capable of engaging an automatic reset safety mechanism 238 positioned toward the distal end of the device body 220. There is also depicted in FIG. 5 a sampling stylet 240 extending from the distal end of the device body and coaxial with it.

Figure 8:
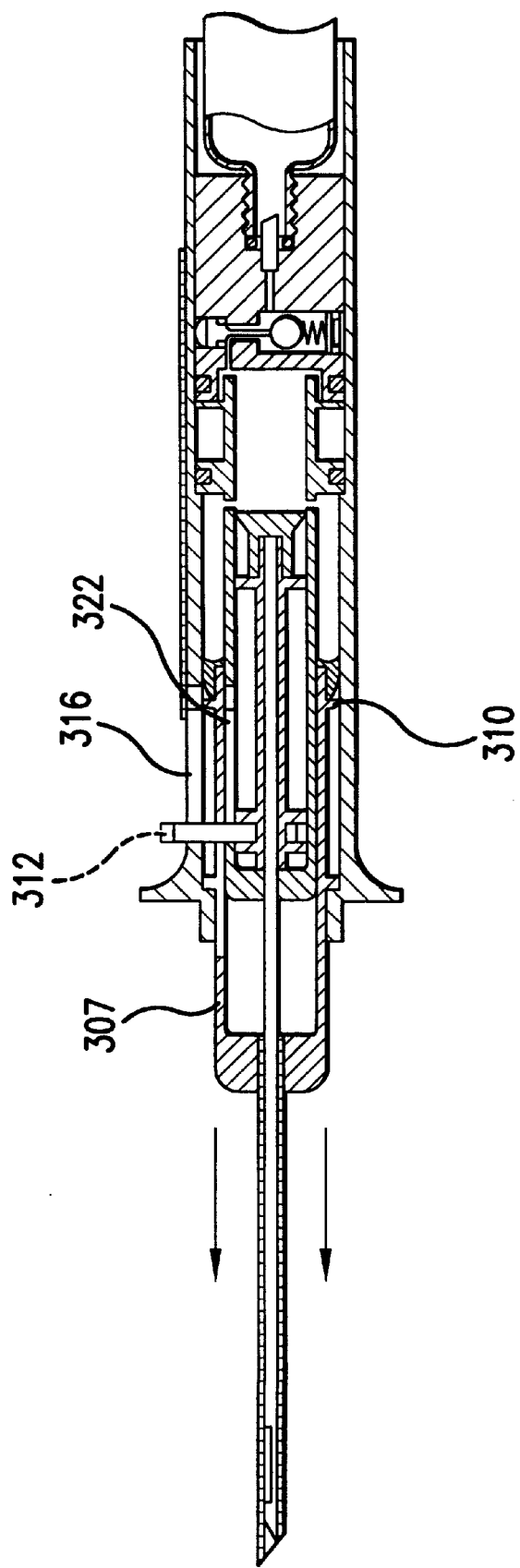
FIG. 8 is a cross-sectional view of an embodiment of the present invention in which both the stylet and the cannula are in a position distal to the housing of the device.

Referring now to FIGS. 6–8, there are depicted section views of an embodiment of the device 210 of the present invention, along the plane 22—22, through the longitudinal axis of the device as indicated from FIG. 5. FIG. 6 is a representation of this embodiment of the present invention in a fully retracted mode wherein the sampling stylet 240 and the cannula 248 are poised for triggering into the selected tissue site. FIG. 7 is a representation of the device after triggering the release of the stylet 240 wherein the stylet is in a fully extended position, but the cannula 248 has not yet been triggered for release. FIG. 8 is a representation of this embodiment of the device wherein both cannula 248 and stylet 240 have been triggered and are in the fully extended position.

Referring now to FIG. 6, the stylet 240 and the cannula 248 constitute a set of piercing and cutting instruments the controlled operation of which enable the sampling of tissue in accord with the practice of the present invention. As can be seen from FIGS. 6–8, stylet 240 and cannula 248 are co-axial and parallel to the long axis of the body 220 of the tissue sampling device 210. In the fully retracted position as shown in FIG. 6, the stylet 240 is retracted completely within the cannula 248 that extends forwardly from the distal end of the housing 220 of the device. Moving attention to the opposite, proximal end of the device, there is shown a valve assembly 253 through which the compressed fluid that drives the actuation of the sampling means of the device enters the device. The valve assembly 253 comprises a cylindrical threaded cartridge receptacle 258 for those embodiments utilizing a carbon dioxide cylinder 225 as the source of compressed fluid, and a lance 262 which serves to pierce the gas cylinder 225 allowing the compressed fluid access to the fluid transfer port 265. The threaded male end of a standard compressed carbon dioxide cylinder threadingly engages the cartridge receptacle 258, and as threaded, it advances sufficiently so that the lance 262 pierces the top seal of the gas cylinder, eventually advancing far enough to seat against the cartridge receptacle o-ring 270.

As seen in FIG. 6, the fluid transfer port 265 comprises a trigger plunger 273, which is engaged by depressing the trigger and which, in turn, acts to displace downwardly a steel ball 275 that is biased upwards by a valve spring 278. As the steel ball is moved downward by the action of the trigger plunger 273, a seal between the ball and the ball valve o-ring 280 is broken. This permits a direct fluid connection between the fluid cartridge 225 and the driving surfaces of the sampling mechanism. Typical commercially available compressed $CO_2$ cartridges contain gas under pressures of approximately 300 psi. Given such pressures, in a normal actuation of the trigger of the device of the invention which consists of a discrete depression of the trigger followed by immediate release, sufficient fluid enters the transfer port 265 to assure that a more than adequate pressure on the internal work surfaces of the device can be generated to effectively complete the sampling sequence. Given the arrangement of seals and valves within the device, if any excess fluid pressure is created within the device during operation, this excess is vented out of the device through the transfer port 265, to and around the trigger plunger 273. In this fashion, none of the excess fluid can reach the patient whose tissue is being sampled via the stylet/cannula assembly. The design of the valve assembly 253 and the transfer port 265 effectively meters the dose of fluid provided to the interior of the device, helping to assure that the compressed fluid is conserved and that, as a consequence, a sufficiently large number of actuations can be achieved from a single, self-contained compressed $CO_2$ cartridge. If the firing trigger 230 is maintained in a depressed state, the fluid continues to flow out of the fluid cylinder through the valve assembly 253. However, any excess fluid is vented out of the transfer port to the atmosphere, and not through stylet/cannula assembly where it could be introduced to the patient.

Upon actuation of the trigger and the subsequent action of the trigger plunger 273 upon the ball valve, the rapidly expanding compressed fluid then flows from the valve assembly 253 through the fluid access channel 284 into the main interior volume of the device 210. Upon expanding through the fluid access channel 284, the released fluid impinges upon the surface of the stylet cup seal 287 at the proximal end of the stylet piston 290. This action of the expanding fluid brings to bear a sufficient force to drive the stylet piston 290 forward through the body 220 of the device in the first step of actuation of the sampling sequence. The stylet piston is driven forward by the expanding fluid's action upon the piston and the cup seal 287 until the forward surface of the annular stylet piston stop 295 engages the inner distal surface of the device housing 298. While the stylet piston 290 moves forward under the compelling force of the expanding fluid, the stylet cup seal 287, being composed of a flexible, elastomeric material, deforms under the pressure of the expanding fluid. As the stylet cup seal deforms, its effective diameter increases creating a fluid-tight seal against the inner surface of the device housing 298. This seal prevents any of the expanded fluid from entering any volumes of the interior of the device body where it could eventually makes its way through the cannula/stylet assembly and into the patient whose tissue is being sampled with the device. Due to the flexibility of the stylet cup seal material, once an actuating sequence has ended and there is no longer any fluid pressure on the seal 287, the seal returns to its undeformed shape thereby reducing its effective outer diameter. This, in turn, allows the stylet/piston assembly to be easily returned to its initial, unextended position within the device body 220. In fact, the force required to return the stylet/piston assembly to its retracted position is substantially less than would have to be exerted against an assembly where the seal between the driving surface of the piston and the remainder of the interior of the body was maintained by a conventional o-ring. This is due to the fact that even when not under pressure, an o-ring provides a continual seal, the force of which will always act counter to any movement of the piston within the body of the device.

Depicted in FIG. 7 is the device in an intermediate stage of the sampling sequence. At this stage, the stylet piston 290 has advanced to its extended position, the extent of which is defined by the action of the stylet piston stop 295. In this position, the stylet 240 has pierced the target tissue to be sampled from the patient, but the cannula 248 has not yet advanced to effectively achieve the desired tissue sampling. As the stylet piston advances to its forward-most position, the expanding fluid gains access to a pair of fluid transfer holes 300 and 300' through the device housing 298. Through these fluid transfer holes, the fluid is able to expand and impinge on the surface of the cannula cup seal 304. This cup seal 304 is annularly disposed about the circumference of the proximal end of the cannula piston 307. The cannula cup seal 304 functions in an identical manner to the stylet cup seal 284, providing a seal between the cannula piston 307 and the inner surface of the cylindrical body 220 of the device. This seal is created through the deformation of the flexible seal material under the effect of the expanding fluid. As with the stylet cup seal, the cannula cup seal 304 assumes a smaller diameter when not deformed under fluid pressure, allowing for easier reset of the cannula/piston assembly to the fully retracted, ready for firing position. Under pressure from the expanding fluid, the cannula piston and, with it, the cannula, are driven forward through the device body 220.

By reference to FIG. 8, it can be seen that the forward, fully-extended position of the cannula piston is limited by the annularly-disposed cannula piston stop 310 against the inside, forward wall of the cylindrical body 220 of the device. The device, as depicted in FIG. 8, is at a stage in the sampling sequence where the automatic, two-stage action of the stylet and cannula are completed, and the stylet and cannula are fully extended within the target tissue site of the patient. The remaining steps in the sampling sequence are done manually. Typically, the health care practitioner performing the sampling operation will remove the sampling device of the invention from the patient with both stylet and cannula in the fully extended position as depicted in FIG. 8. The cannula may next be withdrawn manually by retracting the forward-most portion of the cannula piston 307 that extends proximally from the body 220 of the device when the cannula is in the fully extended position. According to this embodiment of the present invention, it is possible to retract the cannula/piston assembly without affecting the relative position of the stylet/piston assembly. With the stylet in the extended position and the cannula in the retracted position, the sampling notch (not shown) in the stylet is exposed, which position permits removal of the sampled tissue from the device.

By referring back to FIG. 6, the operation of the stylet retractor lever 312 will be apparent. The retractor lever 312 extends vertically upward from the top surface of the body 220 of the device through an L-shaped channel 316 in that top surface. The long dimension of the L-shape of the channel is co-linear with the long axis of the cylindrical body 220 of the device. The stylet retractor lever 312 extends vertically downward through the L-shaped channel 316 that, in turn communicates with a parallel rectangular channel 320 in the cannula piston and which further communicates with a second L-shaped channel 322 through the device housing 298. When properly assembled, the three channels are aligned and co-extensive, permitting access through the assembled device for the retractor lever 312 to reach the stylet piston 290. On the stylet piston, toward the distal end of that piston, there is disposed two parallel annular structures, the stylet piston stop 295, and an annular retractor coupling ring 325. The lower portion of the retractor lever 312 is shaped to irreversibly couple with the surface of the stylet piston between the stylet piston stop 295 and the retractor coupling ring 325. In doing so, this coupling serves two purposes. first, the retractor lever 312 is mechanically coupled to the stylet/piston assembly permitting facile one-fingered retraction of the stylet from its extended position. Secondly, the communication between the channels in the major structures of the device permits the retractor lever to extend through three of the four main structures in the device and directly couple to the fourth. This serves to maintain the separate major components of the device as a comprehensive whole, and prevents the individual components from either going out of alignment or separating from each other.

The stylet retractor lever 312 can serve an additional function as well. By moving the lever 312 in a counter-clockwise fashion into the short dimension of the L-shaped channel 316, the upper portion of the lever 312 becomes positioned immediately below the tip of the device trigger 230. In this position, the lever 312 prevents the trigger 230 from being moved downward and engaging the trigger plunger, effectively acting as a safety catch to prevent unwanted firing of the device.

Figure 9:
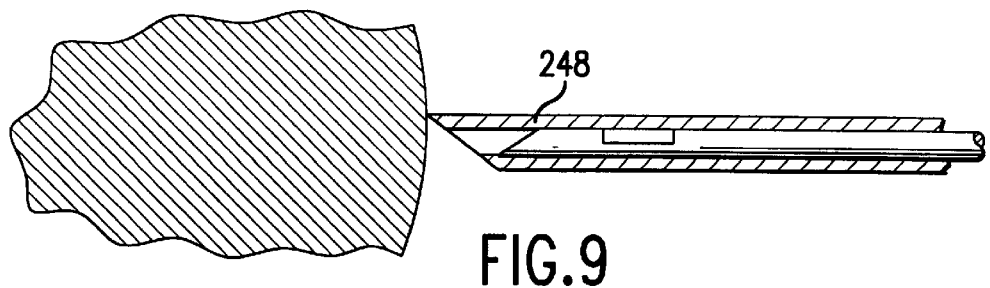
FIG. 9 is a cross-sectional view of the stylet/cannula tip in a ready to sample position.
Figure 10:
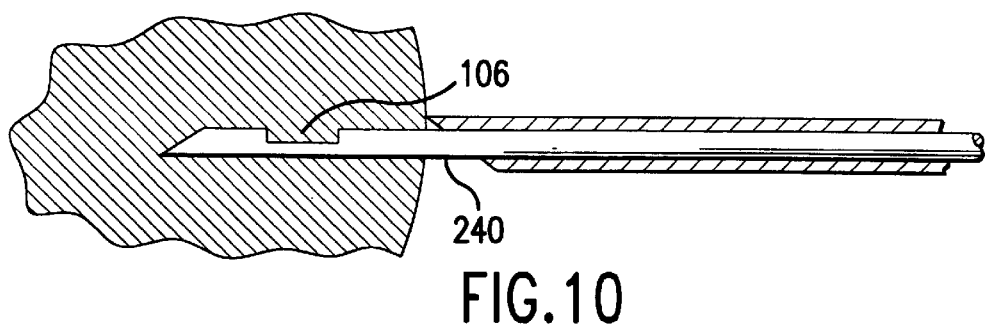
FIG. 10 is a cross-sectional view of the stylet/cannula tip in which the stylet has been extended into the tissue to be sampled.
Figure 11:
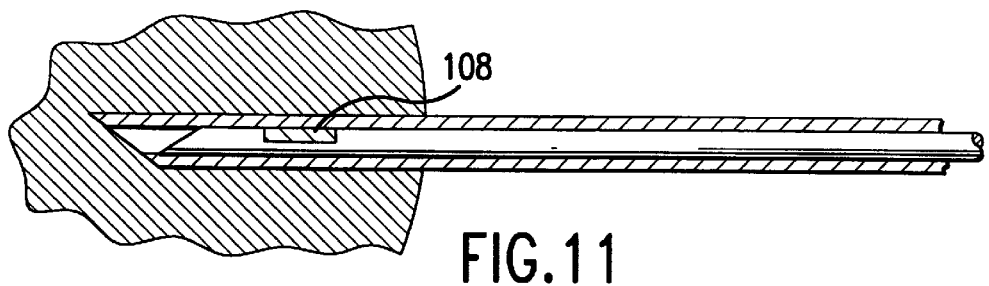
FIG. 11 is a cross-sectional view of the stylet/cannula tip in which the cannula has been extended into the target tissue site.
Figure 12:
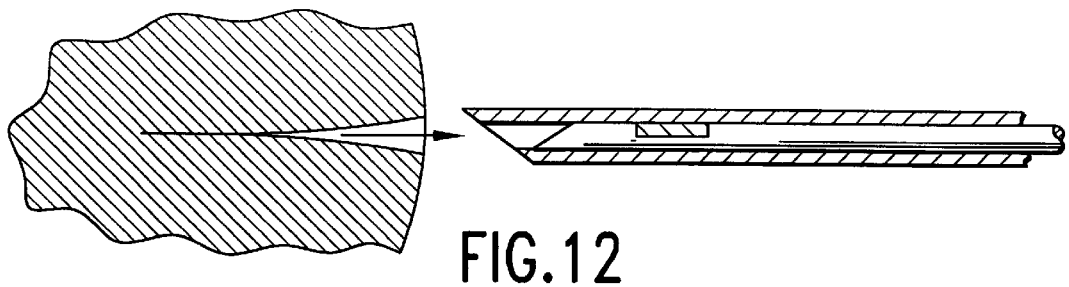
FIG. 12 is a cross-sectional view of the stylet/cannula tip after removal from the target tissue site.
Figure 13:
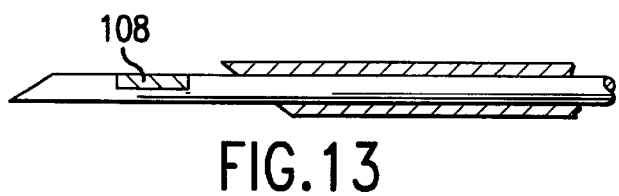
FIG. 13 is a cross-sectional view of the distal stylet/cannula structure showing the cannula in a retracted position wherein sampled tissue is exposed for removal.

The actual tissue sampling operation of the stylet and cannula is depicted in FIGS. 9–13. In FIG. 9, the fully retracted and loaded device 210 is poised on the surface of the patient's skin, presumably having been guided to that position through the aid of a diagnostic imaging device such as an ultrasound image. Upon triggering of the device, the stylet 240 is impelled forward by the action of the expanding fluid on the stylet piston collar, as described above. The sharply angled tip of the stylet easily pierces typical soft tissue. Distally disposed toward the end of the stylet is the stylet tissue notch 106. As the stylet pierces the patient's tissue, a sample portion 108 of the target tissues prolapses into the tissue notch 106 on the stylet 240. This is the situation as depicted in FIG. 10. As the cannula assembly is sequentially impelled distally out of the device, as depicted in FIG. 11, the sharpened leading distal edge of the cannula tip effectively slices through the tissue prolapsed into the stylet tissue notch 106, removing it from surrounding tissue. In this position, the device is withdrawn from the tissue site, as described above and shown in FIG. 12, and the cannula assembly then retracted to expose the tissue in the tissue notch 106, as shown in FIG. 13, for removal and analysis.

It may be of further assistance to the reader who is unfamiliar with such sampling devices as described above and claimed herein to have a more graphic explanation as to how the device may be used in practice. As is well known to the field, a typical use for automatic tissue sampling devices is in conjunction with examination of the prostate by transrectal ultrasonic imaging. Typically the physician inserts into the rectum an ultrasonic probe, and examines the prostate by viewing an ultrasound image on a viewing screen. At this stage the tissue sampling device 210 of the above-described embodiment is not present. If, during this examination, the physician detects a suspicious region for which biopsy is advisable, an attendant is requested to provide the tissue sampling device 210. Typically the attendant opens a sterile pack and provides the device to the physician in unloaded condition, as it comes sterile from the manufacturer. The physician then, while holding the ultrasonic probe so as to maintain the probe in the rectum with one hand (the "ultrasound" hand) grasps the tissue sampling device 210 with the other hand and proceeds to load the device to the firing position. This is accomplished by simply retracting with either thumb or finger the stylet retracting lever 312, and then manually pushing the forward-extending portion of the cannula piston 307 rearward until it, too, is in the fully retracted position. Due to the design of the cup seals, discussed above, the only forces acting to resist these retracting motions are the friction forces created between the cup seals and the surfaces with which they are in contact. This represents a significant advantage over typical spring-driven sampling devices that require the exertion of a considerable amount of force to bring into the cocked or loaded position. The physician has the further option of attaching the device of the invention, through the valve assembly 253 to an external source of compressed fluid either before or after setting the device to the fully retracted position. To accomplish this, the valve assembly 253 merely needs to be designed so that when disconnected from a pressurized fluid source, the coupling is in a closed configuration, as would be readily appreciated by one of skill in the art.

With the device locked or not, as desired, the physician, still using the one "sampling" hand, inserts the sampling device into the rectum through the particular biopsy channel provided by the particular ultrasound probe being employed. This channel may be on the left or right side of the probe of the ultrasonic instrument, or may extend down a channel within the ultrasonic probe. Thus, the needle and the probe can extend closely along-side each other into the rectum.

Thereafter the physician may manipulate the ultrasound device with one hand and the sampling device with the other while watching the viewing screen, until the needle is brought to the desired position. Then, with a finger or thumb of the hand holding the sampling device, depresses the trigger to actuate the device.

Following firing, still with the ultrasonic probe held in position with the physician's "ultrasound" hand, the physician, with the "sampling" hand, withdraws the instrument from the rectum, retracts the cannula and delivers the biopsy specimen to the attendant for immediate transmittal to the laboratory. The physician may now readily repeat the procedure of loading, repositioning and firing the instrument to obtain multiple specimens, all one handedly. When the biopsy procedure is completed, being inexpensively constructed of few, reliable, mostly plastic parts, the instrument may be disposed of in a manner avoiding contaminating or infecting others.

The description above of the device of the present invention and its use has provided detail on the specific aspects of the invention that are useful to the understanding of the full scope of the instantly claimed invention. In doing so, not all elements of any one embodiment have been described in full, particularly where those details are not necessarily essential to the invention and are otherwise within the grasp of those of appropriate level of skill in the relevant art. However, due to the many unique characteristics possessed by embodiments of the present invention, it is possible to utilize the device of the invention in ways not possible with prior art devices. By way of example, and without limitation to the scope of the claimed invention or the range of embodiments available to the invention, there is depicted in FIGS. 14–17 a number of alternative approaches to the use of the device of the invention.

Figure 14:
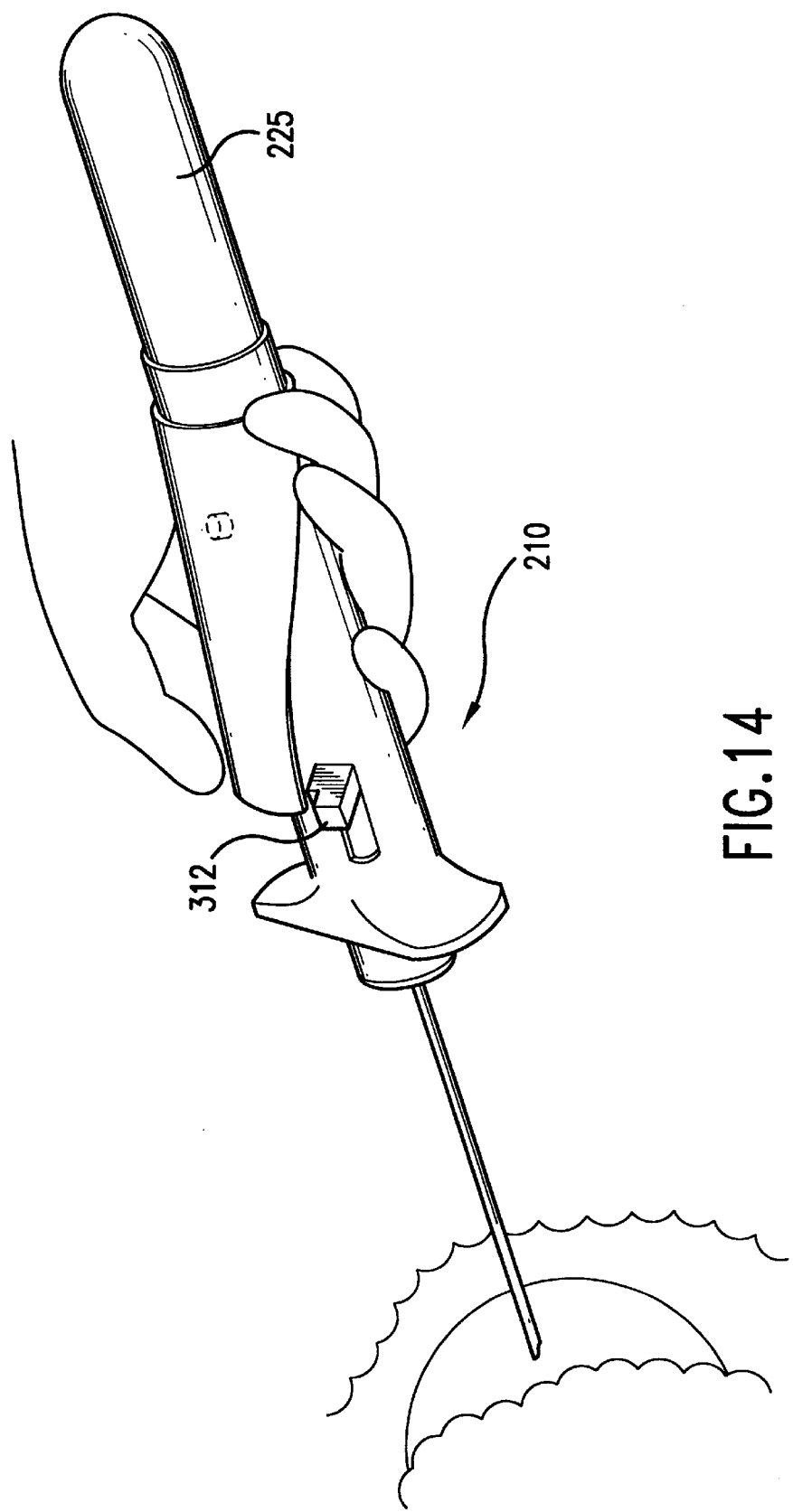
FIG. 14 is an illustration of an embodiment of the present invention.

As shown in FIG. 14, the source of compressed fluid used with the device is a $CO_2$-filled cylinder of zinc-plated mild steel, such as those commonly available for compressed-air guns and bicycle tire inflators. As these cylinders are reasonably small and lightweight, the embodiment pictured in FIG. 14 illustrates a device of the present invention wherein such a cylinder 110 is mounted directly into the housing 220 of the device. Also pictured in FIG. 14 is the firing trigger 230 positioned on the outer surface of the housing 220 of the device so as to be easily reached by the thumb or a finger of the practitioner wielding the device. Due to the limited volume of compressed fluid that the cylinder 110 may contain, it is desirable to minimize the volume of tubing or the means used to bring the fluid from the outlet of the cylinder to the valve assembly 253. Such tubing and connectors can be conventional apparatus readily available and well known to practitioners in the art. It is preferable that, if such a self-contained source of compressed fluid is used, such a container be capable of delivering a plurality of impelling charges to the device. Most preferably, the number of charges would be twenty to thirty.

Figure 15:
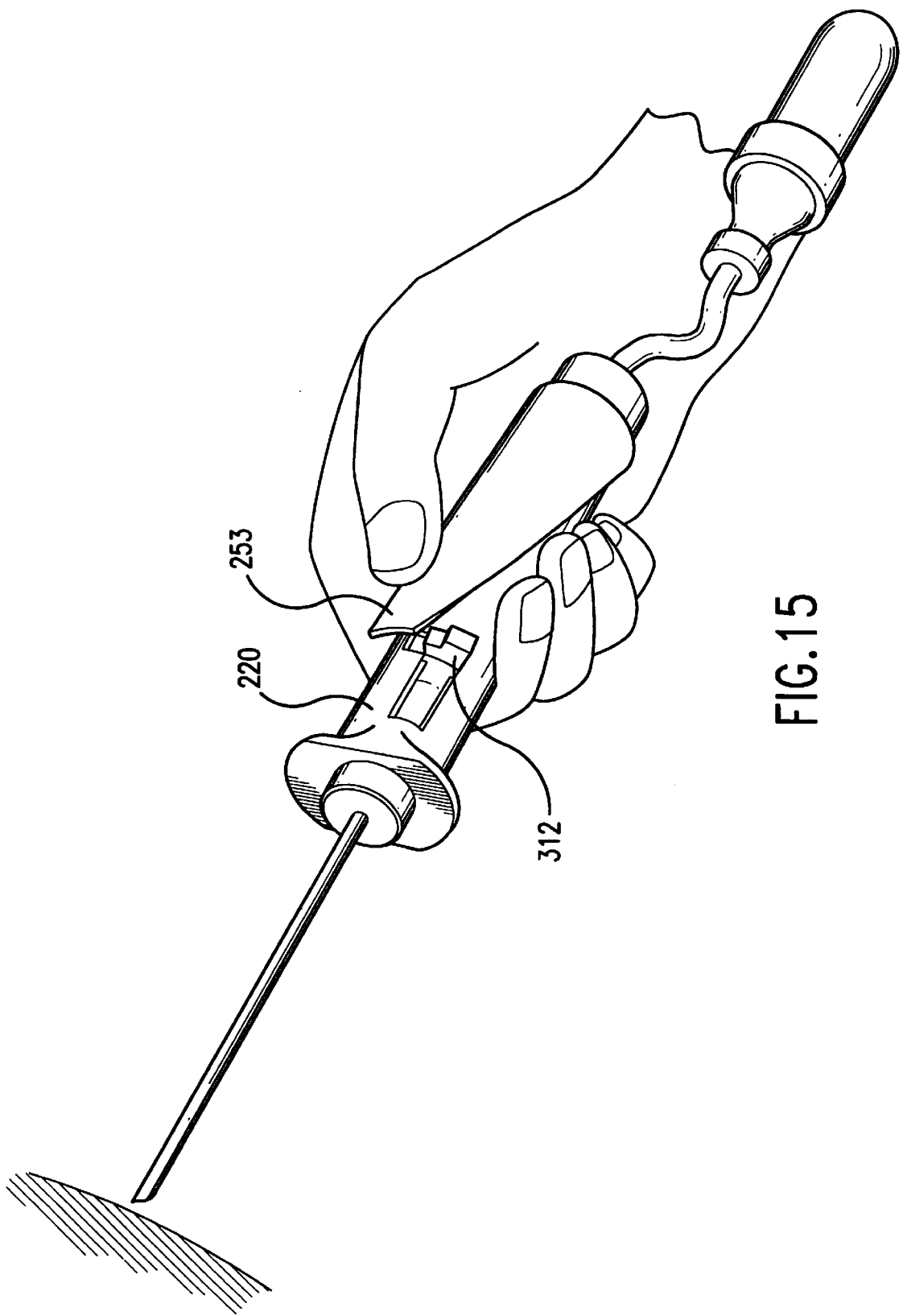
FIG. 15 is an illustration of an alternative embodiment of the present invention.
Figure 16:
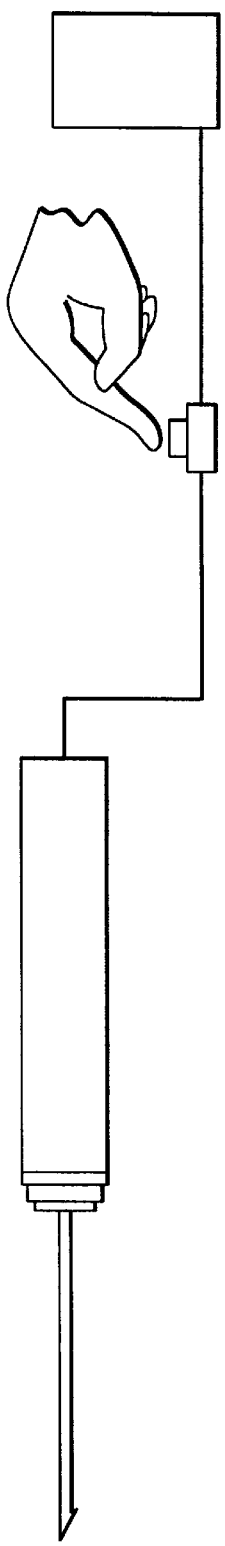
FIG. 16 is an illustration of an alternative embodiment of the present invention.
Figure 17:
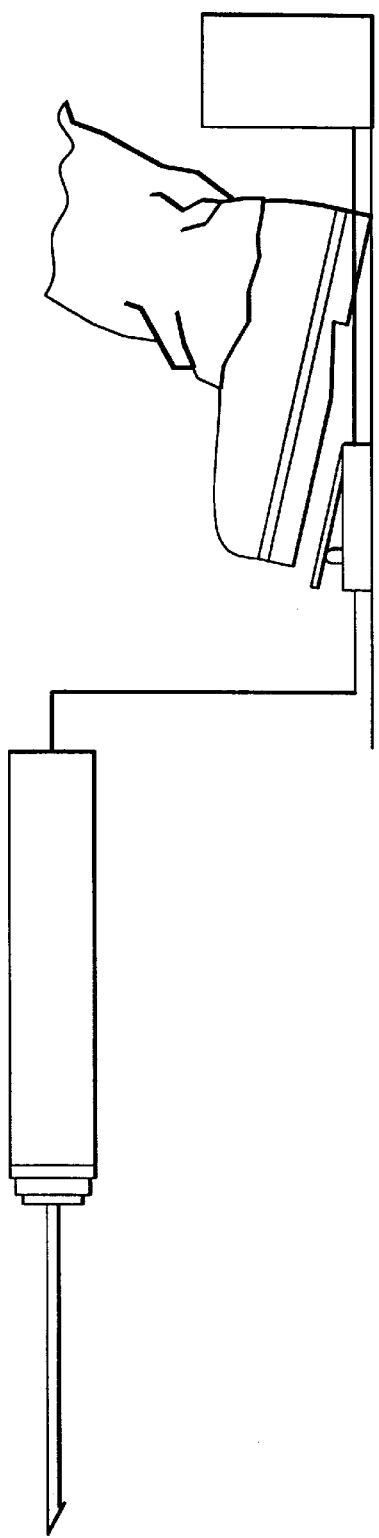
FIG. 17 is an illustration of an alternative embodiment of the present invention.

Illustrated in FIG. 15 is an alternative embodiment wherein the compressed $CO_2$ cylinder 110 is mounted on the hand of the surgeon, and the firing trigger 230 is mounted, as in the previous embodiment, on the surface of the housing 220 of the device. FIGS. 16 and 17 illustrate other alternative embodiments made possible through the unique aspects of the instant invention. In FIG. 16, a large-volume compressed fluid source 120 is depicted. Such source could a be a typical laboratory-sized cylinder of gas such as nitrogen, carbon dioxide or the like. Alternatively, the source of compressed fluid may be centrally located within a facility, and capable of delivering compressed fluid to a number of locations, such as laboratories, operating theaters, examining rooms, out-patient therapy rooms, and the like. Of note in the embodiment of FIG. 16 is that the firing trigger 230 is remote from the sampling device itself. This renders it capable of actuation by a second person, possibly an operating room attendant, in response to direction from the surgeon manipulating the device of the invention. The advantage of this type of embodiment is that the surgeon is given one less element to physically manipulate during use of the device. Once the device is properly positioned, the surgeon need only hold the device steady while waiting for the attendant to respond to his direction and actuate the sampling device.

In an alternative embodiment as depicted in FIG. 17, the firing trigger 230 is in the form of a foot-operated peddle or switch enabling, as in the previously described embodiment, the surgeon to have one less element to handle during manipulation of the device of the invention. The added advantage of this embodiment is that the surgeon need not rely on response to his commands from another party present at the procedure.

Another embodiment of the present invention includes a rotatable handle as shown in FIGS. 18 (top view) and 19 (side view). In this embodiment, the sampling device 210 includes a compact cylinder of compressed gas shown at 225 received by a housing within a handle 500, and a firing trigger 230 which is connecting by a pin hinge 234 to the handle 500. The distal end of the firing trigger 230 is capable of engaging an automatic reset safety mechanism 238 positioned toward the distal end of the handle 500. There is also depicted in FIGS. 18 and 19 a sampling stylet 240 extending from the distal end of a biopsy head portion 501. The handle 500 is rotatable about the head portion 501, and is preferably detachable from the head portion 501. The embodiment shown in FIGS. 18 and 19 differs from the embodiment shown in FIG. 5 in that the embodiment of FIGS. 18 and 19 includes the handle 500 that is rotatably and preferably detachably mounted to the biopsy head portion 501 of the sampling device 210. The handle 500 preferably has a range of motion of at least about 180°, as shown in FIG. 18. The remaining elements of the embodiment shown in FIGS. 18 and 19, including the stylet 240, the cannula 248, and the means for extending the stylet 240 and the cannula 248, are as shown and described for previous embodiments.

The handle 500 is attached to the biopsy head portion 501 by any suitable mechanism, such as a pin hinge 502, which is preferably attached to the handle 500 and fits within a receiving portion 503 of the head portion 501. As shown in cross-section in FIG. 19, the pin hinge arrangement preferably includes static o-ring seals 504. Also shown in cross-section in FIG. 19 is a channel 505 within the head portion 501 to allow for the passage of compressed gas from the cylinder 225 to the head portion 501 to provide the impelling means for extending the stylet 240 and the cannula 248.

The rotatable, detachable handle 500 is useful in a number of applications. For example, biopsy procedures making use of radiological computed tomography ("CT") guidance are complicated by the use of long, heavy biopsy devices. In such procedures, a patient is typically placed within a CT machine to identify the diseased tissue from which a biopsy is desired. Through an iterative process, the patient is removed from the CT machine, a biopsy needle is positioned at the site of the diseased tissue, and the patient is again placed within the CT machine to confirm placement of the biopsy needle at the diseased tissue. Once the location of the diseased tissue is adequately identified, a biopsy is taken. However, biopsy devices with handles are inherently top-heavy and thus may result in the needle inadvertently moving out of an identified target plane for biopsy. In addition, some CT machines have relatively small patient passageways (i.e., gantries), thus preventing the passage of long biopsy devices into the CT machine. The use of the detachable handle 500 remedies these problems in that it can be removed during CT procedures, thus reducing the top-heaviness of the sampling device 210 and also reducing the length of the sampling device 210 so that it more easily fits into small CT machines. After a biopsy position has been identified by CT procedures, the patient is removed from the CT machine, the handle 500 is engaged with the sampling device 210, and the biopsy is taken.

Moreover, modern CT machines often permit "real-time" procedures wherein a physician is able to view the placement of the biopsy needle in-situ. In such procedures, the rotatable handle 500 is particularly useful in that it allows the physician to move the handle out of the plane of view and to take a biopsy while viewing the placement of the biopsy needle. It is thus evident that the use of a rotatable handle 500 in real-time CT results in a considerable savings in terms of both time, cost, and patient comfort.

The removable, rotatable handle 500 is also useful where magnetic resonance imaging ("MRI") procedures are used in conjunction with biopsy procedures. The sampling device 210 is usable with MRI where the head portion 501 is made from non-magnetic materials, and thus can be inserted with a patient into an MRI unit. The handle 500, together with gas cylinder 225, which typically include magnetic materials, are detached from the sampling device 210 while the patient is within the MRI unit, and then reattached following MRI to take a biopsy.

Thus, it should be apparent from these sample embodiments that the unique aspects of the present invention make it possible to utilize the invention in ways not heretofore conceived possible with prior art biopsy devices. As expected, the device of the invention, in a variety of embodiments, may be employed to take biopsy specimens of a variety of soft tissues throughout the body, for example, specimens from the lung, liver, kidney, thyroid, breast or muscle. Due to the greater impelling forces achievable through the use of compressed fluid actuation, it is also possible to sample tissues far denser than those normally accessible to spring-loaded biopsy devices. Using an embodiment of the present invention, it is even possible to "sample" bone from within a patient. Used in this fashion, the compressed fluid device of the present invention can fulfill far more than sampling functions. It is possible to utilize the present invention to create holes in bone or other dense tissue structures within the body even when the tissue extracted or displaced in the creation of these voids is of no particular clinical interest. All that is required in some contemplated applications is to substitute alternative end effectors to appropriate catheter structures in place of the stylet/cannula set associated with conventional soft tissue sampling. In effect, the catheter, or other suitable structure, can be viewed as a transfer mechanism to bring the mechanical forces of the compressed fluid source to bear at sites within a patient's body either not heretofore accessible at all for diagnostic or therapeutic activities, or at a magnitude not before possible. Thus, the present invention provides extended capabilities that can be utilized in surgical procedures more commonly associated with orthopedics and other diverse areas of medical practice than with biopsy sampling.

We claim:

1. A tissue removing device comprising:
    head portion;
    a cannula extending from said head portion, said cannula having a proximal end and a distal end;
    a stylet extending from said head portion, said stylet having a proximal end and a distal end, wherein
        said cannula and said stylet are co-axial with said head portion;
        and said cannula is coaxially disposed about said stylet,
        said stylet is mounted within said head portion for axial movement relative to said head portion and relative to said cannula between a first, retracted position and a second, extended position; and said cannula is mounted within said head portion for axial movement relative to said head portion and relative to said stylet between a first, retracted position and a second, extended position;

a handle rotatably attached to said head portion, said handle containing a compressed fluid passage;

means for impelling said stylet toward said second, extended position in response to an impelling force; and means for impelling said cannula toward said second, extended position in response to an impelling force, wherein said means for impelling said stylet and said means for impelling said cannula are in fluid communication with a single source of compressed fluid, and wherein fluid from said source of compressed fluid provides the impelling force.

2. The tissue removing device of claim 1, wherein said handle is rotatable over at least about 180 degrees.

3. The tissue removing device of claim 2, wherein said handle is rotatable over about 360 degrees.

4. The tissue removing device of claim 1, wherein said handle is removably attached to said head portion.

5. The tissue removing device of claim 4, wherein
said handle includes a pin hinge;
said head portion includes a receiving portion having a mating configuration to said pin hinge; and
said handle is attached to said head portion by placing said pin hinge into said head portion.

6. The tissue removing device of claim 5, further comprising an o-ring between said handle and said head portion when said handle is attached to said head portion.

7. The tissue removing device of claim 1, wherein said stylet comprises a circumferential notch near its distal end.

8. The tissue removing device of claim 1, wherein said handle includes a housing for receiving said source of compressed fluid.

9. The tissue removing device of claim 8, further comprising a firing trigger on said handle that releases the fluid from said source of compressed fluid.

10. The tissue removing device of claim 9, wherein said head portion includes a channel to allow the fluid from said source of compressed to pass into said head portion.

11. The tissue removing device of claim 1, wherein said compressed fluid is carbon dioxide gas.

12. The tissue removing device of claim 1, wherein said compressed fluid is an inert gas.

13. The tissue removing device of claim 1, wherein said means for impelling said stylet comprises:
a stylet shaft connected to the proximal end of said stylet, wherein at least a portion of said stylet shaft is disposed within said head portion;
a stylet shaft collar mounted on the portion of said stylet shaft disposed within said head portion.

14. The tissue removing device of claim 13, wherein
said head portion comprises a first cavity and a second cavity in sequence along the longitudinal axis of said head portion, wherein the inner diameter of said first cavity is approximately equal to the outer diameter of said stylet shaft collar, and wherein the inner diameter of said second cavity is greater than the outer diameter of said stylet shaft collar.

15. The tissue removing device of claim 14, wherein at least one surface of said stylet shaft collar is beveled.

16. The tissue removing device of claim 14, further comprising an o-ring disposed circumferentially around the outer walls of said stylet shaft collar.

17. The tissue removing device of claim 1, wherein said means for impelling said cannula comprises:

a cannula shaft connected to the proximal end of said cannula, said cannula shaft being extendable from said head portion;
a cannula shaft collar mounted on a portion of said cannula shaft disposed within said head portion.

18. The tissue removing device of claim 17, further comprising an o-ring disposed circumferentially around the outer walls of said cannula shaft collar.

19. A tissue removing device comprising:
a head portion;
a cannula extending from said head portion, said cannula having a proximal end and a distal end;
a stylet extending from said head portion, said stylet having a proximal end and a distal end, wherein
said cannula and said stylet are co-axial with said head portion;
said cannula is coaxially disposed about said stylet,
said stylet is mounted within said head portion for axial movement relative to said head portion and relative to said cannula between a first, retracted position and a second, extended position; and
said cannula is mounted within said head portion for axial movement relative to said head portion and relative to said stylet between a first, retracted position and a second, extended position;
a handle removeably coupled to said head portion, said handle containing a compressed fluid passage; and
a single source of compressed fluid, wherein fluid from said source of compressed fluid provides an impelling force for impelling said stylet toward said second, extended position and for impelling said cannula toward said second, extended position.

20. The tissue removing device of claim 19, wherein said handle is rotatable over at least about 180 degrees.

21. The tissue removing device of claim 19, wherein said handle is removably attached to said head portion.

22. A tissue removing device comprising:
a housing defining a compressed fluid cavity;
a cannula protruding from said housing, said cannula having a proximate end and a distal end;
a stylet protruding from said housing, said stylet having a proximate end and a distal end;
wherein
said stylet is mounted for axial movement relative to said housing and relative to said cannula between a first, retracted position and a second, extended position; and
said cannula is mounted for axial movement relative to said housing and relative to said stylet between a first, retracted position and a second, extended position;
means for impelling said stylet toward said second, extended position in response to an impelling force;
means for impelling said cannula toward said second, extended position in response to an impelling force; and
said means for impelling said stylet and said means for impelling said cannula are in fluid communication with a single source of compressed fluid, and wherein fluid from said source of compressed fluid provides the impelling force.

23. The tissue removing device of claim 22, wherein said compressed fluid is carbon dioxide gas.

24. The tissue removing device of claim 22, wherein said compressed fluid is an inert gas.

25. The tissue removing device of claim 22, further comprising a firing trigger for releasing the fluid from said source of compressed fluid into said housing.

26. The tissue removing device of claim 25, wherein the firing trigger is positioned on a surface of said housing.

27. The tissue removing device of claim 25, wherein the firing trigger is remote from said housing.

28. The tissue removing device of claim 22, wherein the impelling force is between approximately 5 and 25 pounds.

29. The tissue removing device of claim 22, wherein said stylet comprises a circumferential notch near its distal end.

30. The tissue removing device of claim 22, further comprising:
   a first finger-displaceable member for retracting said stylet from said second, extended position to said first, retracted position; and
   a second finger-displaceable member for retracting said cannula from said second, extended position to said first, retracted position.

31. The tissue removing device of claim 22, wherein said means for impelling said stylet comprises:
   a stylet shaft connected to the proximate end of said stylet, wherein at least a portion of said stylet shaft is disposed within said housing;
   a stylet shaft collar mounted on the portion of said stylet shaft disposed within said housing.

32. The tissue removing device of claim 31, wherein
   said housing comprises a first cavity and a second cavity in sequence along the longitudinal axis of said housing, wherein the inner diameter of said first cavity is approximately equal to the outer diameter of said stylet shaft collar, and wherein the inner diameter of said second cavity is greater than the outer diameter of said stylet shaft collar.

33. The tissue removing device of claim 32, wherein at least one surface of said stylet shaft collar is beveled.

34. The tissue removing device of claim 32, further comprising an o-ring disposed circumferentially around the outer walls of said stylet shaft collar.

35. The tissue removing device of claim 22, wherein said means for impelling said cannula comprises:
   a cannula shaft connected to the proximate end of said cannula, said cannula shaft being extendable from said housing;
   a cannula shaft collar mounted on a portion of said cannula shaft disposed within said housing.

36. The tissue removing device of claim 35, further comprising an o-ring disposed circumferentially around the outer walls of said cannula shaft collar.

37. A tissue removing device comprising:
   a head portion;
   a cannula extending from said head portion, said cannula having a proximal end and a distal end;
   a stylet extending from said head portion, said stylet having a proximal end and a distal end, wherein
      said cannula and said stylet are co-axial with said head portion;
      said cannula is coaxially disposed about said stylet,
      said stylet is mounted within said head portion for axial movement relative to said head portion and relative to said cannula between a first, retracted position and a second, extended position; and
      said cannula is mounted within said head portion for axial movement relative to said head portion and relative to said stylet between a first, retracted position and a second, extended position;
   a handle rotatably attached to said head portion;
   means for impelling said stylet toward said second, extended position in response to an impelling force; and
   means for impelling said cannula toward said second, extended position in response to an impelling force.

38. A tissue removing device comprising:
   a housing defining a compressed fluid cavity;
   a cannula protruding from said housing, said cannula having a proximate end and a distal end;
   a stylet protruding from said housing, said stylet having a proximate end and a distal end, wherein said cannula is coaxially disposed about said stylet;
   wherein
      said stylet is mounted for axial movement relative to said housing and relative to said cannula between a first, retracted position and a second, extended position; and
      said cannula is mounted for axial movement relative to said housing and relative to said stylet between a first, retracted position and a second, extended position; and
   a single source of compressed fluid, wherein said compressed fluid provides an impelling force for impelling said stylet and said cannula toward their respective said second, extended positions.

39. The tissue removing device of claim 38, wherein said compressed fluid is an inert gas.

40. The tissue removing device of claim 38, wherein the impelling force is between approximately 5 and 25 pounds.

41. A tissue removing device comprising:
   a housing defining a compressed fluid cavity;
   a cannula protruding from said housing, said cannula having a proximate end and a distal end, said cannula supported by said housing and adapted to move between a first position and a second position, said cannula in fluid communication with said compressed fluid cavity;
   a stylet located within said cannula, said stylet having a proximate end and a distal end, said stylet supported by said housing within said cannula, said stylet adapted to move between a retracted position and an extended position, said stylet in fluid communication with said compressed fluid cavity; and
   a source of compressed fluid in communication with said compressed fluid cavity.

42. The tissue removing device of claim 41 wherein said source of compressed fluid is removably coupled to said housing.

43. The tissue removing device of claim 41 wherein said stylet and said cannula move axially along the axial centerline of said housing.

* * * * *